US010912842B2

(12) United States Patent
Sutherland et al.

(10) Patent No.: US 10,912,842 B2
(45) Date of Patent: Feb. 9, 2021

(54) CD123 ANTIBODIES AND CONJUGATES THEREOF

(71) Applicant: SEATTLE GENETICS, INC., Bothell, WA (US)

(72) Inventors: May Kung Sutherland, Bothell, WA (US); Lori Westendorf, Snohomish, WA (US); Django Sussman, Seattle, WA (US)

(73) Assignee: Seattle Genetics, Inc., Bothell, WA (US)

(*) Notice: Subject to any disclaimer, the term of this patent is extended or adjusted under 35 U.S.C. 154(b) by 301 days.

(21) Appl. No.: 15/735,738

(22) PCT Filed: Jun. 9, 2016

(86) PCT No.: PCT/US2016/036631
§ 371 (c)(1),
(2) Date: Dec. 12, 2017

(87) PCT Pub. No.: WO2016/201065
PCT Pub. Date: Dec. 15, 2016

(65) Prior Publication Data
US 2018/0169261 A1    Jun. 21, 2018

Related U.S. Application Data

(60) Provisional application No. 62/175,121, filed on Jun. 12, 2015.

(51) Int. Cl.
| | |
|---|---|
| *A61K 47/68* | (2017.01) |
| *C07K 16/28* | (2006.01) |
| *A61K 31/5513* | (2006.01) |
| *A61K 31/5517* | (2006.01) |
| *A61P 35/02* | (2006.01) |
| *A61P 35/00* | (2006.01) |
| *C07K 16/30* | (2006.01) |
| *A61K 39/00* | (2006.01) |

(52) U.S. Cl.
CPC ...... *A61K 47/6849* (2017.08); *A61K 31/5513* (2013.01); *A61K 31/5517* (2013.01); *A61K 47/6803* (2017.08); *A61K 47/6851* (2017.08); *A61P 35/00* (2018.01); *A61P 35/02* (2018.01); *C07K 16/2866* (2013.01); *C07K 16/30* (2013.01); *A61K 2039/505* (2013.01); *C07K 2317/14* (2013.01); *C07K 2317/21* (2013.01); *C07K 2317/24* (2013.01); *C07K 2317/52* (2013.01); *C07K 2317/56* (2013.01); *C07K 2317/73* (2013.01); *C07K 2317/92* (2013.01)

(58) Field of Classification Search
CPC ............ A61K 47/6803; A61K 31/5513; A61K 31/5517; A61K 47/6849; A61K 47/6851; C07K 16/2866; A61P 35/00; A61P 35/02
See application file for complete search history.

(56) References Cited

U.S. PATENT DOCUMENTS

| | | | |
|---|---|---|---|
| 7,960,516 B2 * | 6/2011 | Matheus | C07K 16/2863 530/387.3 |
| 8,920,803 B2 | 12/2014 | Drane et al. | |
| 2012/0189540 A1 | 7/2012 | Bergstein | |
| 2014/0227173 A1 | 8/2014 | Eberhart et al. | |

FOREIGN PATENT DOCUMENTS

| | | | |
|---|---|---|---|
| WO | WO2009/007427 A2 | 1/2009 | |
| WO | WO2009/070844 A1 | 6/2009 | |
| WO | WO2011/100786 A1 | 8/2011 | |
| WO | WO2011/130613 A1 | 10/2011 | |
| WO | WO-2012021934 A1 * | 2/2012 | ......... C07K 16/2866 |
| WO | WO2013/008171 A1 | 1/2013 | |
| WO | WO2013/173496 A2 | 11/2013 | |
| WO | WO2014/057119 A1 | 4/2014 | |
| WO | WO2014/138805 A1 | 9/2014 | |
| WO | WO2014/165119 A1 | 10/2014 | |
| WO | WO2015/026892 A1 | 2/2015 | |
| WO | WO2016/201065 A1 | 12/2016 | |

OTHER PUBLICATIONS

Howard et al, Bioorganic and Medicinal Chemistry Letters, 2009, vol. 19, pp. 6463-6466 (Year: 2009).*
Smith (Toxicological Sciences, 2009, vol. 110, pp. 4-30) (Year: 2009).*
Meyer et al, Biochemical and Biophysical Research Communications, 2018, vol. 499, pp. 594-599 (Year: 2018).*
PCT Application No. PCT/US2016/036631, Search Report and Written Opinion dated Sep. 13, 2016, 14 pages.
Broughton, et al., "Dual Mechanism of Interleukin-3 Receptor Blockade by an Anti-Cancer Antibody", Cell Reports 8, pp. 410-419, (Jul. 24, 2014).
Busfield, et al., "Targeting of acute myeloid leukemia in vitro and in vivo with an anti-CD123 mAb engineered for optimal ADCC", Leukemia, pp. 1-9, (2014).
Li, et al., Author Manuscript "Characterization of SGN-CD123A, a potent CD123-directed antibody-drug conjugate for acute myeloid leukemia", Mol Cancer Ther, AACR, Available at: http://mct.aacrjournals.org/, 32 pages, (Nov. 15, 2017).

(Continued)

*Primary Examiner* — Karen A. Canella
(74) *Attorney, Agent, or Firm* — Seattle Genetics, Inc.

(57) ABSTRACT

The invention provides murine, chimeric, and humanized antibodies that specifically bind to CD123 and conjugates thereof.

53 Claims, 6 Drawing Sheets
Specification includes a Sequence Listing.

(56) References Cited

OTHER PUBLICATIONS

Nievergall, et al., "Monoclonal antibody targeting of IL-3 receptor a with CSL362 effectively depletes CML progenitor and stem cells" Blood, vol. 123, No. 8, pp. 1218-1228, (Feb. 2014).

Sutherland, et al., "SGN-CD33A: a novel CD33-targeting antibody-drug conjugate using a pyrrolobenzodiazepine dimer is active in models of drug-resistant AML", Blood, 22, vol. 122, No. 8, pp. 1455-1463, (Aug. 2013).

Sutherland, et al., "SGN-CD 123A, a Pyrrolobenzodiazepine Dimer Linked AntiCD123 Antibody Drug Conjugate, Demonstrates Effective Anti-Leukemic Activity in Multiple Preclinical Models of AML", Blood, vol. 126, iss. 23, p. 330, (Dec. 2015).

Larkin, et al., "Larkin et al., Novel Theraies in AML Reason for Hope or Just Hype?", 2014 ASCO Educational Book, pp. e341-e351, Available at: asco.org/edbook, (Dec. 31, 2014).

Kurella, et al., "Structure guided homology model based design and engineering of mouse antibodies for humanization", Bioinformation, 10(4), pp. 180-186, (2014).

\* cited by examiner

|  | 2 | 19 | 21 | 22 | 38 | Differences with human FW |
|---|---|---|---|---|---|---|
| LA | F | F | A | I | N | L | 2 |
| LB | F | V | M | S | L | 5 |

Bold type is human
Non-bold type is mouse

```
                         10         20         30         40         50         60         70
                ....|....|....|....|....|....|....|....|....|....|....|....|....|....|
SEQ ID NO:9
7G3MS  vL       DFVMTQSPSSLTVTAGEKVTMSCKSSQSLLNSGNQKNYLTWYLQKPGQPPKLLIYWASTRESGVPDRFTG
IGKV4-1/IGKJ2   ....I.....D..A.SL..RA.IN.....V.Y.S.N...A.Q..............S.
h7G3MS vLA      ..........D..A.SL..RA.IN.....V.Y.S.N...A.Q..............S.
h7G3MS vLB      ..........D..A.SL..R.................................S.

80         90        100        110
                ....|....|....|....|....|....|....|....|....|....|
7G3MS  vL       SGSGTDFTLTISSVQAEDLAVYYCQNDYSYPYTFGGGTKLEIKR
IGKV4-1/IGKJ2   ..............L.....V....QY..T...Q.........
h7G3MS vLA      ..............L.....V........T...Q.........
h7G3MS vLB      ..............L.....V............Q.........
```

Fig. 6

SEQUENCE LISTING

<160> NUMBER OF SEQ ID NOS: 15

<210> SEQ ID NO 1
<211> LENGTH: 120
<212> TYPE: PRT
<213> ORGANISM: Artificial
<220> FEATURE:
<223> OTHER INFORMATION: Heavy chain variable region for HC

<400> SEQUENCE: 1

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120

```
<210> SEQ ID NO 2
<211> LENGTH: 114
<212> TYPE: PRT
<213> ORGANISM: Artificial
<220> FEATURE:
<223> OTHER INFORMATION: Light chain variable region for LA

<400> SEQUENCE: 2

Asp Phe Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg

<210> SEQ ID NO 3
<211> LENGTH: 450
<212> TYPE: PRT
<213> ORGANISM: Artificial
<220> FEATURE:
<223> OTHER INFORMATION: Heavy chain for HC with mutant IgG1 having a
      cysteine substitution at position 239, according to the EU index
      as set forth in Kabat

<400> SEQUENCE: 3

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Cys Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 4
<211> LENGTH: 220
<212> TYPE: PRT
<213> ORGANISM: Artificial
<220> FEATURE:
<223> OTHER INFORMATION: Light chain for LA

<400> SEQUENCE: 4

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

```
Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 5
<211> LENGTH: 329
<212> TYPE: PRT
<213> ORGANISM: Artificial
<220> FEATURE:
<223> OTHER INFORMATION: mutant heavy chain constant region (having a
      cysteine substitution at position 239, according to the EU index
      as set forth in kabat)

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 6
<211> LENGTH: 329
<212> TYPE: PRT
<213> ORGANISM: Artificial
<220> FEATURE:
<223> OTHER INFORMATION: Naturally occurring heavy chain constant region

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 7
<211> LENGTH: 106
<212> TYPE: PRT
<213> ORGANISM: Artificial
<220> FEATURE:
<223> OTHER INFORMATION: Light chain constant region

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 120
<212> TYPE: PRT
<213> ORGANISM: Artificial
<220> FEATURE:
<223> OTHER INFORMATION: murine 7G3 antibody heavy chain variable region

<400> SEQUENCE: 8

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ser Ser Thr Ala Tyr
65                  70                  75                  80

Met His Leu Asn Ser Leu Thr Ser Glu Asp Ser Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ala
            115                 120
```

```
<210> SEQ ID NO 9
<211> LENGTH: 114
<212> TYPE: PRT
<213> ORGANISM: Artificial
<220> FEATURE:
<223> OTHER INFORMATION: murine 7G3 antibody light chain variable region

<400> SEQUENCE: 9

Asp Phe Val Met Thr Gln Ser Pro Ser Ser Leu Thr Val Thr Ala Gly
1               5                   10                  15

Glu Lys Val Thr Met Ser Cys Lys Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Arg

<210> SEQ ID NO 10
<211> LENGTH: 5
<212> TYPE: PRT
<213> ORGANISM: Artificial
<220> FEATURE:
<223> OTHER INFORMATION: amino acid sequence of CDR-H1 of humanized 7G3

<400> SEQUENCE: 10

Asp Tyr Tyr Met Lys
1               5

<210> SEQ ID NO 11
<211> LENGTH: 17
<212> TYPE: PRT
<213> ORGANISM: Artificial
<220> FEATURE:
<223> OTHER INFORMATION: amino acid sequence of CDR-H2 of humanized 7G3

<400> SEQUENCE: 11

Asp Ile Ile Pro Ser Asn Gly Ala Thr Phe Tyr Asn Gln Lys Phe Lys
1               5                   10                  15

Gly

<210> SEQ ID NO 12
<211> LENGTH: 11
<212> TYPE: PRT
<213> ORGANISM: Artificial
<220> FEATURE:
<223> OTHER INFORMATION: amino acid sequence of CDR-H3 of humanized 7G3

<400> SEQUENCE: 12

Ser His Leu Leu Arg Ala Ser Trp Phe Ala Tyr
1               5                   10

<210> SEQ ID NO 13
<211> LENGTH: 17
<212> TYPE: PRT
```

```
<213> ORGANISM: Artificial
<220> FEATURE:
<223> OTHER INFORMATION: amino acid sequence of CDR-L1 of humanized 7G3

<400> SEQUENCE: 13

Lys Ser Ser Gln Ser Leu Leu Asn Ser Gly Asn Gln Lys Asn Tyr Leu
1               5                   10                  15

Thr

<210> SEQ ID NO 14
<211> LENGTH: 7
<212> TYPE: PRT
<213> ORGANISM: Artificial
<220> FEATURE:
<223> OTHER INFORMATION: amino acid sequence of CDR-L2 of humanized 7G3

<400> SEQUENCE: 14

Trp Ala Ser Thr Arg Glu Ser
1               5

<210> SEQ ID NO 15
<211> LENGTH: 9
<212> TYPE: PRT
<213> ORGANISM: Artificial
<220> FEATURE:
<223> OTHER INFORMATION: amino acid sequence of CDR-L3 of humanized 7G3

<400> SEQUENCE: 15

Gln Asn Asp Tyr Ser Tyr Pro Tyr Thr
1               5
```

CD123 ANTIBODIES AND CONJUGATES THEREOF

CROSS REFERENCE TO RELATED APPLICATIONS

This application is a U.S. national stage filing under 35 U.S.C. 371 of International Application No. PCT/US2016/036631, filed Jun. 9, 2016, which claims the benefit of U.S. Provisional Patent Application No. 62/175,121, filed Jun. 12, 2015, which is incorporated herein by reference in its entirety.

REFERENCE TO A SEQUENCE LISTING

This application includes an electronic sequence listing in a file named IL3R-00211US_Sequence Listing_ST25.txt, created on Nov. 14, 2017 and containing 19 KB, which is hereby incorporated by reference.

BACKGROUND

CD123 is the 70 kD protein transmembrane alpha chain of the IL-3 receptor and is also referred to as IL3R-alpha. CD123 is known to be expressed on primary AML samples and has been reported on a number of malignant cells. The present invention provides CD123 antibodies and conjugates thereof.

SUMMARY OF THE CLAIMED INVENTION

Provided herein are anti-CD123 antibodies and CD123 directed antibody-drug conjugates. In particular, provided herein are CD123 directed pyrrolobenzodiazepine ("PBD") antibody-drug conjugates and methods of using such conjugates to treat CD123 expressing disorders. Preferred anti-CD123 antibodies are chimeric or humanized forms of the murine 7G3 antibody (Sun et al., Blood, 1996, 87(1):83-92). The murine 7G3 antibody comprises a heavy chain variable region having the amino acid sequence set forth in SEQ ID NO:8 and a light chain variable region having the amino acid sequence set forth in SEQ ID NO:9. Preferred humanized 7G3 antibodies for use herein are antibodies constructed using the human germline sequence hIGHv1-2 and J exon $J_H$-1 for the heavy chain variable region and the human germline sequence hIGKv4-1 and J exon $J_K$-2 for the light chain variable regions. Particularly preferred humanized 7G3 antibodies comprise the heavy chain variable region set forth in SEQ ID NO:1 and the light chain variable region set forth in SEQ ID NO:2.

Antibodies for use in the present invention can be intact antibodies or antigen binding fragments thereof. The humanized 7G3 antibody can have a mature heavy chain variable region that is fused to a heavy chain constant region and a mature light chain variable region that is fused to a light chain constant region. The heavy chain constant region can be a naturally occurring or mutant form of a human constant region (e.g., SEQ ID NO:5, a heavy chain IgG1 constant region with cysteine substituting for serine at position 239, (S239C) or SEQ ID NO:6). The heavy chain constant region can be of IgG1 isotype. An exemplary light chain constant region amino acid sequence is set forth in SEQ ID NO:7

The chimeric or humanized 7G3 antibodies described herein are conjugated to drug-linkers, including PBD drug-linkers to provide CD123 antibody-drug conjugates. Attachment can be via conventional or site specific conjugation methods. An exemplary attachment is via an engineered cysteine at position 239 of the heavy chain constant region, according to the EU index as set forth in Kabat. The CD123 directed antibody-drug conjugates are used to treat CD123 expressing disease, including CD123 expressing cancers, such as AML.

In other embodiments, the chimeric or humanized 7G3 antibodies described herein are conjugated to drug-linkers, including glucuronide-pegylated MMAE drug-linkers to provide CD123 antibody-drug conjugates.

In a further embodiment, the drug-linker attached to the humanized 7G3 antibody has the formula:

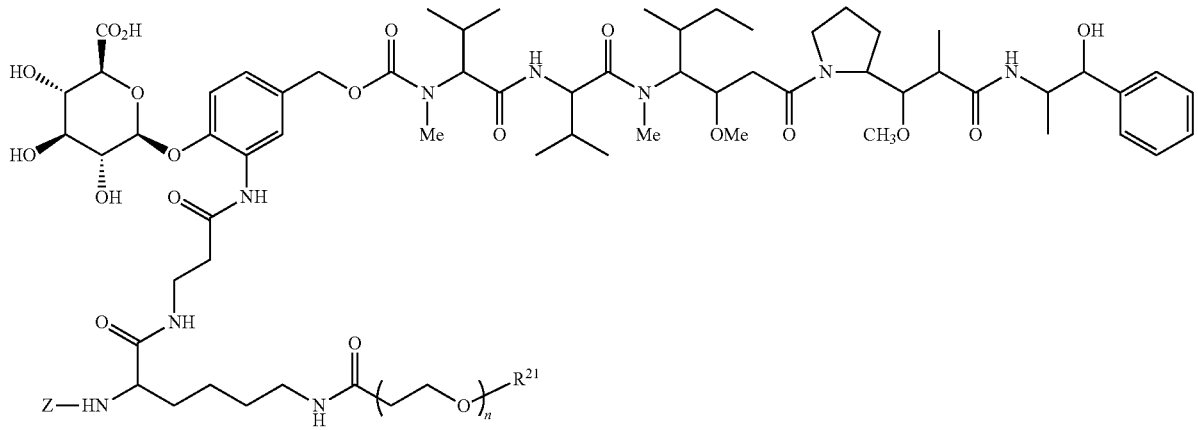

or a pharmaceutically acceptable salt thereof wherein Z represents an organic moiety having a reactive site capable of reacting with a functional group on the antibody to form a covalent attachment thereto, n ranges from 8 to 36, $R^{PR}$ is hydrogen or a protecting group, $R^{21}$ is a capping unit for the polyethylene glycol moiety.

In some embodiments of this disclosure, the value n can range from 8 to 14. In other embodiment of this disclosure, the value n ranges from 10 to 12. In a further embodiment of this disclosure, the value of n is 12. In another embodiment, $R^{21}$ is —$CH_3$ or —$CH_2CH_2CO_2H$.

In another embodiment, any of the disclosed pegylated-MMAE antibody-drug conjugates has a p value of 8. In another embodiment, the drug-linker is attached to the antibody via the cysteine residues of the interchain disulfide bonds of the antibody.

BRIEF DESCRIPTION OF THE FIGURES

FIG. 6 shows the amino acid sequences for the light chain variable region of the murine 7G3 antibody and the humanized vLA, and vLB, light chain and selected human germline acceptor variable region sequences.

DEFINITIONS

Figure 1:
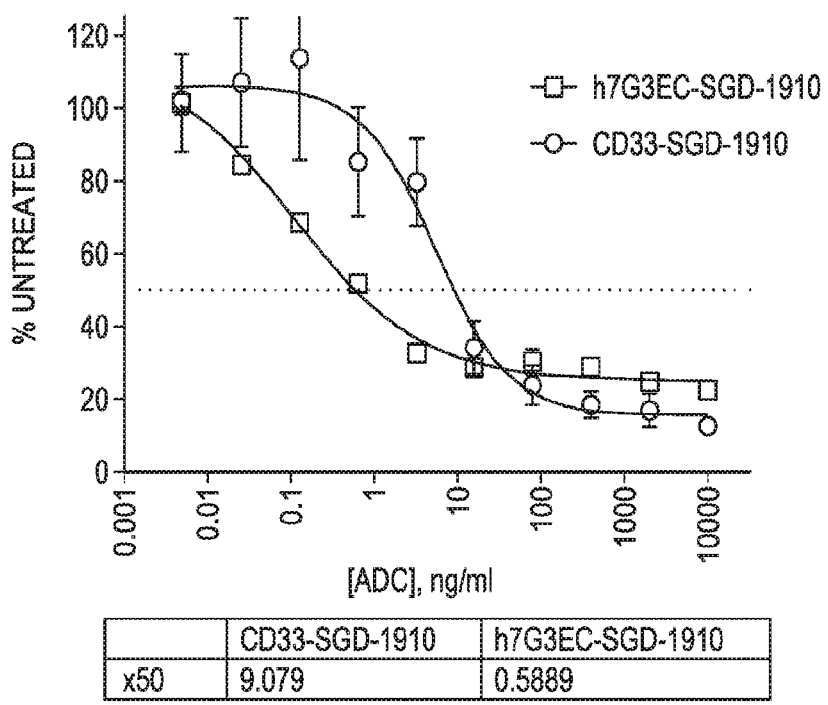
FIG. 1 shows the result of an in vitro cytotoxicity assay testing the humanized 7G3ec SGD-1910 antibody-drug conjugate against a MDR+-positive AML cell line, KG-1, that expresses low copies of CD123 in comparison to CD33. Despite the low copy number, the h7G3ec SGD-1910 antibody-drug conjugate showed potent activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, for example, U.S. Pat. No. 4,816,567). The "monoclonal antibodies" may also be isolated from phage antibody libraries using the techniques described in Clackson et al. (1991) *Nature,* 352:624-628 and Marks et al. (1991) *J. Mol. Biol.,* 222:581-597, for example or may be made by other methods. The antibodies described herein are monoclonal antibodies.

Antibodies are typically provided in isolated form. This means that an antibody is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least 60%, 70%, 80%, 90%, 95 or 99% w/w pure of interfering proteins and contaminants from production or purification. Antibodies, including isolated antibodies, can be conjugated to cytotoxic agents and provided as antibody drug conjugates.

An "isolated" polynucleotide refers to a polynucleotide that has been identified and separated and/or recovered from components of its natural.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. The CD123 directed antibody-drug conjugates and anti-CD123 antibodies specifically bind to CD123.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the subscript and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes). The mature variable regions of each light/heavy chain pair form the antibody binding site. Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering system) in which corresponding residues between different heavy chain variable regions or between different light chain variable regions are assigned the same number. Numbering of the heavy chain constant region is via the EU index as set forth in Kabat (Kabat, *Sequences of Proteins of Immunological Interest* (National Institutes of Health, Bethesda, Md., 1987 and 1991).

The term "antibody" includes intact antibodies and antigen binding fragments thereof. An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof. Antibody fragments compete with the intact antibody from which they were derived for specific binding to the target including separate heavy chains, light chains Fab, Fab', $F(ab')_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$—$V_H$—$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "therapeutically effective amount" or 'effective amount" refers to an amount of the antibody-drug conjugate that is effective to treat a disease or disorder in a mammal. In the case of cancer, a therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit tumor growth; and/or relieve one or more of the symptoms associated with the cancer. For cancer therapy, efficacy can, for example, be measured by assessing the time to disease progression (TTP) and/or determining the response rate (RR). The term "effective regimen" refers to a combination of amount of the conjugate being administered and dosage frequency adequate to accomplish treatment of the disorder.

The terms "treat" or "treatment," unless otherwise indicated by context, refer to therapeutic treatment wherein the object is to inhibit or slow down (lessen) an undesired physiological change or disorder, such as the development or spread of cancer. Beneficial or desired clinical results include, but are not limited to, alleviation of symptoms, diminishment of extent of disease, a stabilized (i.e., not worsening) state of disease, delay or slowing of disease progression, amelioration or palliation of the disease state, and remission (whether partial or complete), whether detectable or undetectable. "Treatment" can also mean prolonging survival as compared to expected survival if not receiving treatment. Those in need of treatment include those with detectable disease. Those in need of treatment can also include those with undetectable disease, e.g., patients that have achieved a complete response after treatment for the CD123 expressing disorder but are in need of therapy in order to prevent relapse.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD123 antibody or antibody-drug conjugate is administered to a subject.

The phrase "pharmaceutically acceptable salt," refers to pharmaceutically acceptable organic or inorganic salts. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Solvates in the context of the invention are those forms of the compounds of the invention that form a complex in the solid or liquid state through coordination with solvent molecules. Hydrates are one specific form of solvates, in which the coordination takes place with water. Preferred solvates in the context of the present invention are hydrates.

Unless otherwise apparent from the context, the term "about" encompasses values within a standard deviation of a stated value.

DETAILED DESCRIPTION

I. General

The present invention is based, in part, on the discovery that antibody-drug conjugates, including PBD antibody-drug conjugates targeted to CD123 are particularly effective at killing CD123+ expressing cells. In particular, it was found that a high affinity 7G3 humanized antibody could be constructed using as the heavy chain variable region acceptor sequence, the germline hIGHv1-2 and J exon $J_H$-1, and for the light chain variable region acceptor sequence, the germline hIGKv4-1 and J exon $J_K$-2, and by mutating residues at one or more key sites back to the murine antibody or murine germline sequence. For the heavy chain, these key sites included one or more of positions H20, H38, H48, H66, H67, H69, H71, H73, H81, H82A, and H93. For the light chain, these key sites included one or more of positions L2, L19, L21, L22 and L38. Notably, the high affinity 7G3 humanized antibody was constructed without the need for performing affinity maturation and while retaining the identity of the CDRs of the murine antibody. The high affinity 7G3 humanized antibody was also effective at drug delivery as part of an antibody drug conjugate. When conjugated to a SGD-1910 PBD drug-linker, the resultant h7G3ec PBD conjugate was highly active against a panel of AML cell lines and primary AML samples irrespective of low CD123 copy number and MDR+ status. The "ec" designation following h7G3 indicates that the antibody has a cysteine substitution at position 239 of the heavy chain (numbering is by the EU index as set forth in Kabat)

II. Target Molecules

Unless otherwise indicated, CD123 and IL-3R alpha are used interchangeably and refer to human CD123 or IL-3R alpha. An exemplary human sequence is assigned UniProtKB/Swiss-Prot Accession Number—P26951.

III. Antibodies of the Invention

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence.

Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and diabodies, a humanized antibody typically comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than 3 conservative amino acid substitutions in each CDR. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical. In some humanized antibodies of the present invention, there are at least six murine 7G3 backmutation in the heavy chain variable framework region of the antibody and at least two murine 7G3 backmutations in the light chain variable region of the antibody.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., *J. Immunol.* 169:3076, 2002; Vajdos et al., *Journal of Molecular Biology*, 320: 415-428, 2002; Iwahashi et al., *Mol. Immunol.* 36:1079-1091, 1999; Tamura et al, *Journal of Immunology*, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

The invention provides antibodies directed against the CD123 antigen. Preferred antibodies are chimeric or humanized antibodies derived from the murine 7G3 antibody. A preferred acceptor sequence for the heavy chain variable region is the germline $V_H$ exon hIGHv1-2 and for the J exon ($J_H$), exon $J_H$-1. For the light chain variable region, a preferred acceptor sequence is exon hIGKv4-1 and for the J exon $J_K$-2

An exemplary anti-CD123 antibody is a humanized antibody that includes the heavy chain CDRs as set forth in SEQ ID NO:1 and the light chain CDRs as set forth in SEQ ID NO:2 and additionally has a mature heavy chain variable region with at least 90%, 91%, 92%, 93%, 94% or 95% identity to SEQ ID NO:1 and a mature light chain variable region with at least 90%, 91%, 92%, 93%, 94% or 95% identity to SEQ ID NO:2. The CDRs are as defined by Kabat. Preferably, the following amino acid residues of the heavy chain variable domain framework are maintained: H48 is occupied by I, H67 is occupied by A, H69 is occupied by L, H71 is occupied by V, H73 is occupied by R, H93 is occupied by T and the following amino acid residues of the light chain are maintained: L2 is occupied by F, L38 is occupied by L. In some aspects, the following amino acid residues of the heavy chain are maintained: H20 is occupied by M, H38 is occupied by K, H48 is occupied by I, H66 is occupied by K, H67 is occupied by A, H69 is occupied by L, H71 is occupied by V, H73 is occupied by R, H81 is occupied by H, H82A is occupied by N, and H93 is occupied by T and the following amino acid residues of the light chain variable domain framework are maintained: L2 is occupied by F, L38 is occupied by L. In some aspects, the following amino acid residues of the heavy chain variable domain framework are present: H20 is occupied by M or V, H38 is occupied by K or R, H48 is occupied by I, H66 is occupied by K or R, H67 is occupied by A, H69 is occupied by L, H71 is occupied by V, H73 is occupied by R, H81 is occupied by E or H, H82A is occupied by S or N, and H93 is occupied by T and the following amino acid residues of the light chain variable domain framework are present: L2 is occupied by F, L19 is occupied by A or V, L21 is occupied by I or M, L22 is occupied by N or S, L38 is occupied by L.

Accordingly, provided herein are humanized antibodies that comprise a heavy chain variable region as set forth in SEQ ID NO:1 and a light chain variable region as set forth in SEQ ID NO:2 provided that H20 is occupied by M or V, H38 is occupied by K or R, H48 is occupied by I, H66 is occupied by K or R, H67 is occupied by A, H69 is occupied by L, H71 is occupied by V, H73 is occupied by R, H81 is occupied by E or H, H82A is occupied by S or N, and H93 is occupied by T and the following amino acid residues of the light chain are present: L2 is occupied by F, L19 is occupied by A or V, L21 is occupied by I or M, L22 is occupied by N or S, and L38 is occupied by L.

Humanized forms of the mouse m7G3 antibody include three exemplified humanized heavy chain mature variable regions (HA-HC) and two exemplified humanized light chain mature variable regions (LA-LB). The permutations of these chains include HALA, HALB, HBLA, HBLB, HCLA and HCLB. Of these permutations, HCLA is preferred. HCLA comprises the heavy chain set forth in SEQ ID NO:1 and light chain set forth in SEQ ID NO:2. Any one of HALA, HALB, HBLA, HBLB, and HCLB can be used, however, in place of HCLA.

In some aspects, the apparent dissociation constant (kd) of the humanized 7G3 antibodies for human CD123 is preferably within a range of 0.1 nM to 10 nM, even more preferably within a range of 0.1 nM to 5 nM, even preferably within a range of 1 nM to 3 nM or 2 nM to about 3 nM. In some aspect, the antibodies of the present invention have an apparent dissociation constant within a range of 0.1 to 1.5 times, or even 0.5 to 2 times that of the apparent dissociation constant of the murine 7G3 antibody for human CD123. In some aspects, the apparent dissociation constant (kd) of the antibodies for human CD123 is about 2.7.

A. Selection of Constant Region

Heavy and light chain variable regions of humanized 7G3 antibodies can be linked to at least a portion of a human constant region. The choice of constant region can depend, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 has weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain subscript domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

The constant region can be modified to allow for site specific conjugation of a drug-linker. Such techniques include the use of naturally occurring or engineered cysteine residues, disulfide bridges, poly-histidine sequences, glyco-engineering tags, and transglutaminase recognition sequences. An exemplary substitution for site specific conjugation using bacterial transglutaminase is N297S or N297Q. An exemplary substitution for site specific conjugation using an engineered cysteine is S239C. Antibody fragments can also be modified for site-specific conjugation of a drug-linker, see for example, Kim et al., *Mol Cancer Ther* 2008; 7(8).

B. Expression of Recombinant Antibodies

Humanized or chimeric 7G3 antibodies can be produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, *From Genes to Clones*, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NSO. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Once expressed, antibodies can be purified according to standard procedures of the art, including HPLC purification, column chromatography, gel electrophoresis and the like (see generally, Scopes, *Protein Purification* (Springer-Verlag, NY, 1982)).

IV. Nucleic Acids

The invention further provides nucleic acids encoding any of the humanized heavy and light chains described herein. Typically, the nucleic acids also encode a signal peptide fused to the mature heavy and light chain variable regions. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In one embodiment, this disclosure provides an isolated polynucleotide encoding an antibody heavy chain variable region comprising the amino acid sequence as set forth in HA, HB, or HC. For example, the isolated polynucleotide can encode an antibody heavy chain variable region comprising the amino acid sequence of SEQ ID NO:1. This isolated polynucleotide can further encode a human IgG heavy chain constant region. The isotype of the IgG constant region is, e.g., IgG1, IgG2, IgG3, or IgG4. In one embodiment, the isotype of the IgG constant region is IgG1. In another embodiment, the encoded IgG1 constant region has an amino acid sequence comprising a substitution at residue 239, according to the EU index as set forth in Kabat system, i.e., S239C. The disclosure also provides an expression vector comprising the isolated polynucleotide encoding the antibody heavy chain variable region comprising the amino acid sequence as set forth in HA, HB, or HC (e.g., SEQ ID NO:1 or variants thereof), and further, a host cell comprising that expression vector. In some embodiments, the host cell is a mammalian host cell, e.g., a CHO cell.

In another embodiment, this disclosure provides an isolated polynucleotide encoding an antibody light chain variable region comprising the amino acid sequence as set forth in LA or LB. For example, an isolated polynucleotide encoding an antibody light chain variable region comprising the amino acid sequence of SEQ ID NO:2. This isolated polynucleotide can further encode a human IgG light chain constant region. The isotype of the IgG light chain constant region is, e.g., a kappa constant region. The disclosure also provides an expression vector comprising the isolated polynucleotide encoding the antibody light chain variable region comprising the amino acid sequence as set forth in LA or LB (e.g., SEQ ID NO:2 or variants thereof), and further, a host cell comprising that expression vector. In some embodiments, the host cell is a mammalian host cell, e.g., a CHO cell.

In another embodiment, this disclosure provides an isolated polynucleotide or polynucleotides encoding an antibody heavy chain variable region comprising the amino acid sequence of SEQ ID NO:1 and an antibody light chain variable region comprising the amino acid sequence of SEQ ID NO:2, the heavy chain variable domain and the light chain variable domain forming an antibody or antigen binding fragment that specifically binds to human CD123. This disclosure also provides an expression vector comprising the isolated polynucleotide or polynucleotides the encode the antibody heavy chain variable region comprising the amino acid sequence of SEQ ID NO:1 and the antibody light chain variable region comprising the amino acid sequence of SEQ ID NO:2. A host cell comprising the expression vector or vectors is also provided. The host cell is preferably a mammalian cell, e.g., a CHO cell.

In another embodiment, this disclosure provides first and second vectors comprising a polynucleotide encoding an antibody heavy chain variable region comprising the amino acid sequence of SEQ ID NO:1 and a polynucleotide encoding an antibody light chain variable region comprising the amino acid sequence of SEQ ID NO:2, the heavy chain variable domain and the light chain variable domain forming an antibody or antigen binding fragment that specifically binds to human CD123. Host cell comprising the vectors are provided, preferably mammalian host cells, such as a CHO cell.

V. Antibody-Drug Conjugates

Anti-CD123 antibodies can be conjugated to cytotoxic moieties or cytostatic moieties to form antibody-drug conjugates (ADCs). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-CD123 antibody can be conjugated to a cytotoxic agent such as a chemotherapeutic agent, or a toxin (e.g., a cytostatic or cytocidal agent such as, for example, abrin, ricin A, pseudomonas exotoxin, or diphtheria toxin). Examples of useful classes of cytotoxic agents include, for example, DNA minor groove binders, DNA alkylating agents, and microtubule disrupting agents. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4]benzodiazepines, indolinobenzodiazepines, and oxazolidinobenzodiazepines) and vinca alkaloids. Exemplary antibody-drug conjugates include auristatin based antibody-drug conjugates meaning that the drug component is an auristatin drug, maytansinoid antibody-drug conjugates meaning that the drug component is a maytansinoid drug, and benzodiazepine antibody drug conjugates meaning that the drug component is a benzodiazepine (e.g., pyrrolo[1,4]benzodiazepines, indolinobenzodiazepines, and oxazolidinobenzodiazepines).

Techniques for conjugating therapeutic agents to antibodies, are well-known. (See, e.g., Alley et al., Current Opinion in Chemical Biology 2010 14:1-9; Senter, Cancer J., 2008, 14(3):154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the CD123-expressing cancer cell but is not substantially sensitive to the extracellular environment, such that the conjugate is cleaved from the antibody when it is internalized by the CD123-expressing cancer cell (e.g., in the endosomal or, for example by virtue of pH sensitivity or protease sensitivity, in the lysosomal environment or in the caveolear environment). In some aspects, the therapeutic agent can also be attached to the antibody with a non-cleavable linker.

The present inventors have found a CD123 targeted ADC comprising a PBD drug-linker is particularly effective for treating CD123-expressing disorders.

A preferred PBD for use in the present invention is as follows:

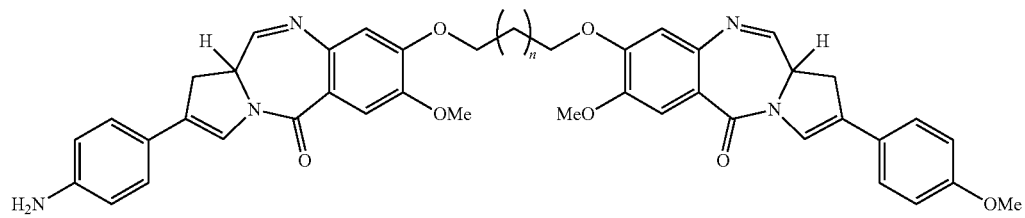

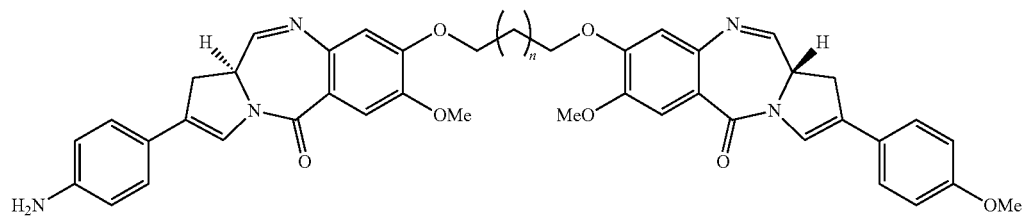

or a pharmaceutically salt, solvate, or solvate of the salt; wherein the subscript n is 1 or 3.

A preferred PBD drug-linker for use in the present invention is represented by Formula I below:

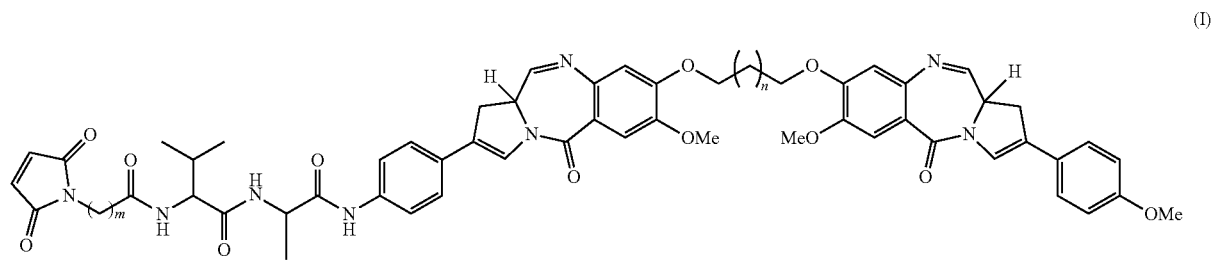

(I)

or a pharmaceutically salt, solvate, or solvate of the salt; wherein the subscript n is 1 or 3 and the subscript m is an integer from 2 to 5.

The preferred stereochemistry of the PBD drug component of the drug-linker is as shown in Formula Ia below:

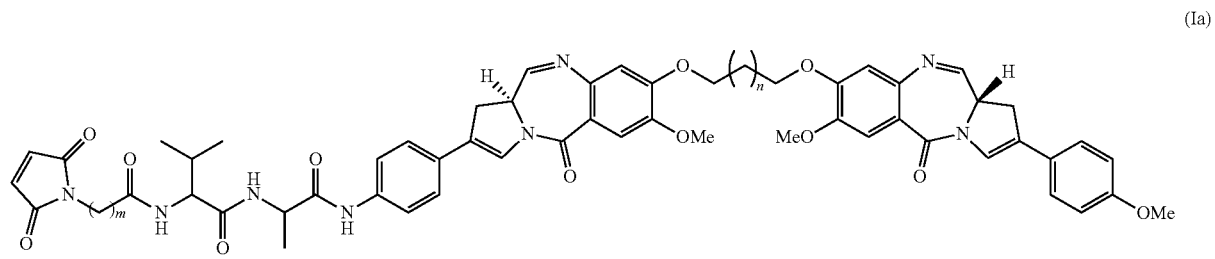

(Ia)

The preferred stereochemistry of the PBD drug and linker components of the SGD-1910 PBD drug-linker is as shown in Formula Ib below:
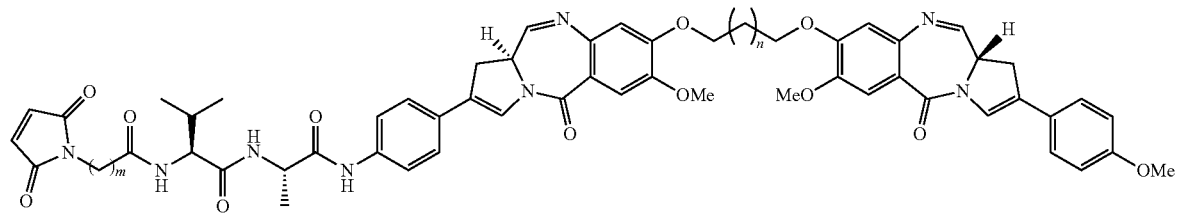
(Ib)
The PBD drug-linker is conjugated to a humanized CD123 antibody of the present invention to produce a CD123 targeted antibody-drug conjugate as shown below in formulas II, IIa, and IIb
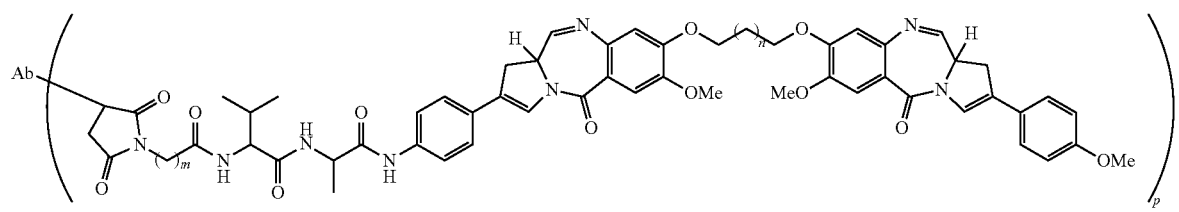
(II)
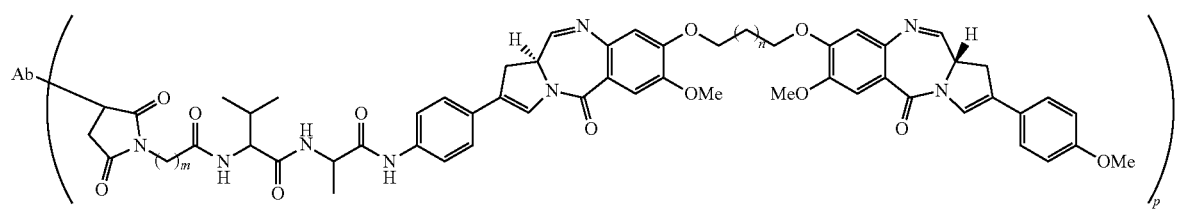
(IIa)
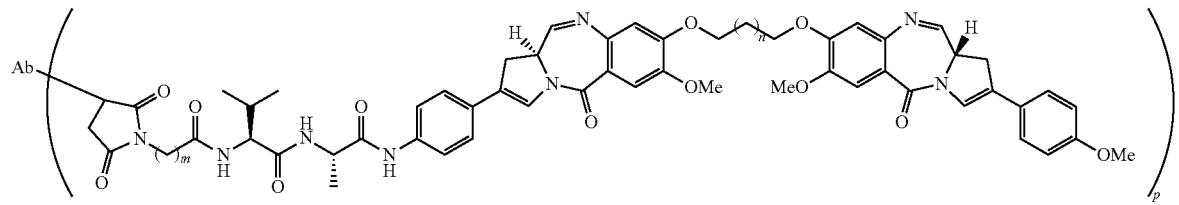
(IIb)

or a pharmaceutically salt, solvate, or solvate of the salt; wherein the subscript n is 1 or 3; the subscript m is an integer from 2 to 5; and the subscript p is an integer from 1 to 4.

Exemplary drug-linkers include MMAE drug-linkers. Incorporation of a polyethylene glycol polymer as a side chain into a cleavable β-glucuronide MMAE drug-linker provides antibody drug-conjugates with decreased plasma clearance and increased antitumor activity in xenograft models as compared to a non-PEGylated control. Accordingly, particularly advantageous drug-linkers for attachment to the antibodies of the present invention are as follows:

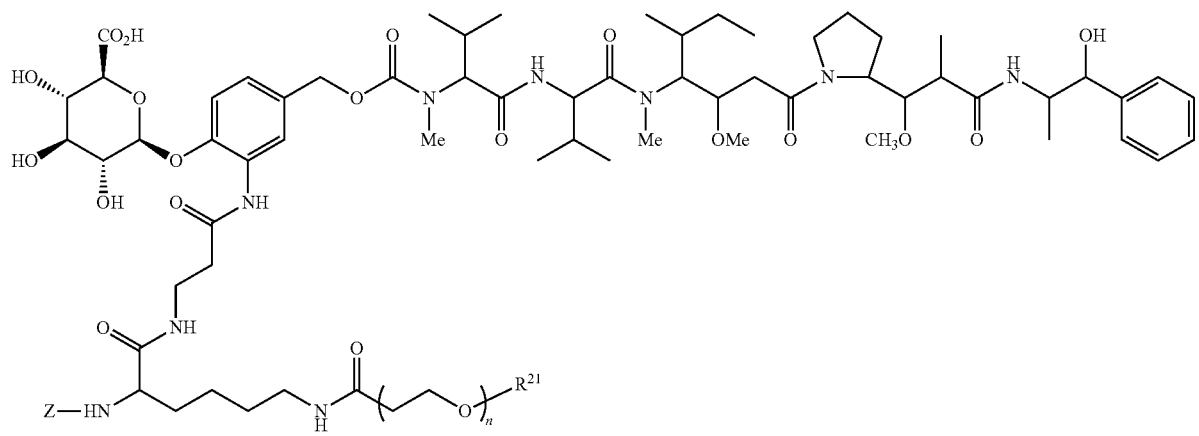

(V)

or a pharmaceutically acceptable salt thereof.

A preferred stereochemistry for such drug-linker is shown below:

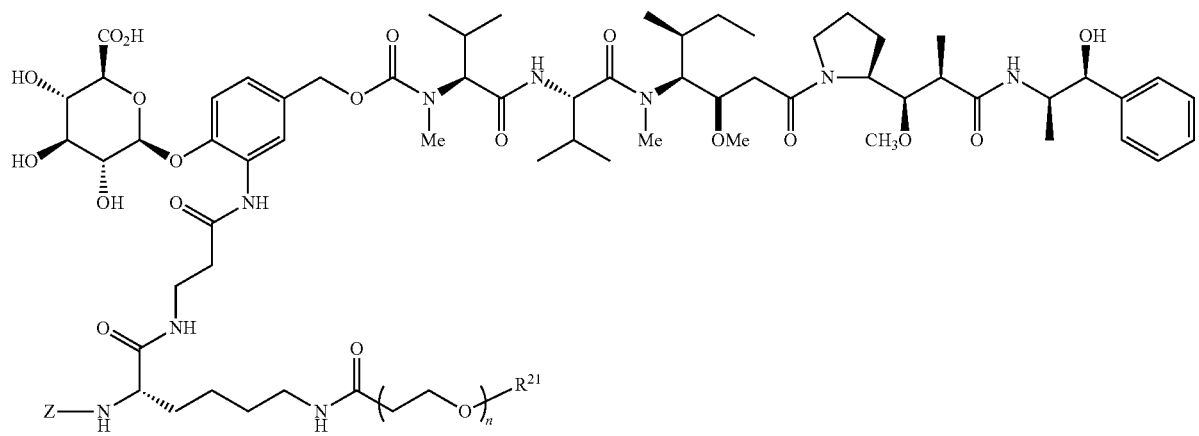

(Va)

or a pharmaceutically acceptable salt thereof wherein for formulas V and Va, Z represents an organic moiety having a reactive site capable of reacting with a functional group on the antibody to form a covalent attachment thereto, n ranges from 8 to 36 and most preferably ranges from 8 to 14 (most preferably 12), $R^{21}$ is a capping unit for the polyethylene glycol moiety, preferably —$CH_3$ or —$CH_2CH_2CO_2H$.

A preferred Z moiety is a maleimido-containing moiety. Particularly preferred Z moieties are shown in the drug-linkers below:

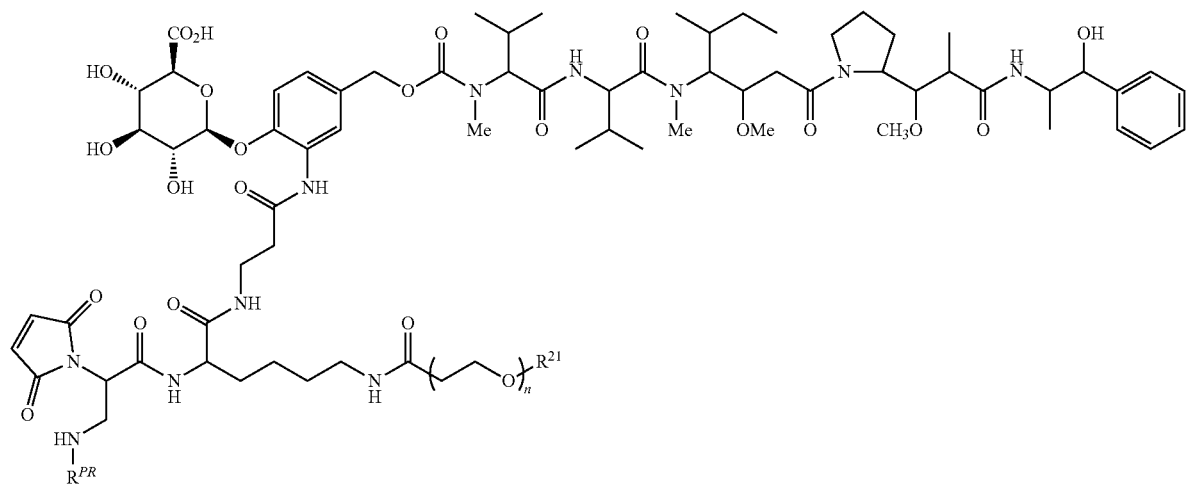

(VI)

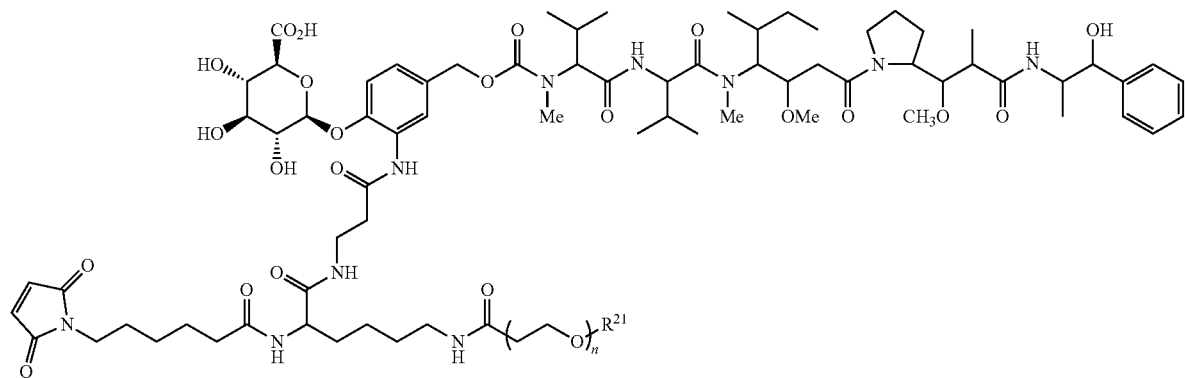

(VII)

or a pharmaceutically acceptable salt thereof.

A preferred stereochemistry for such drug-linkers is shown below:

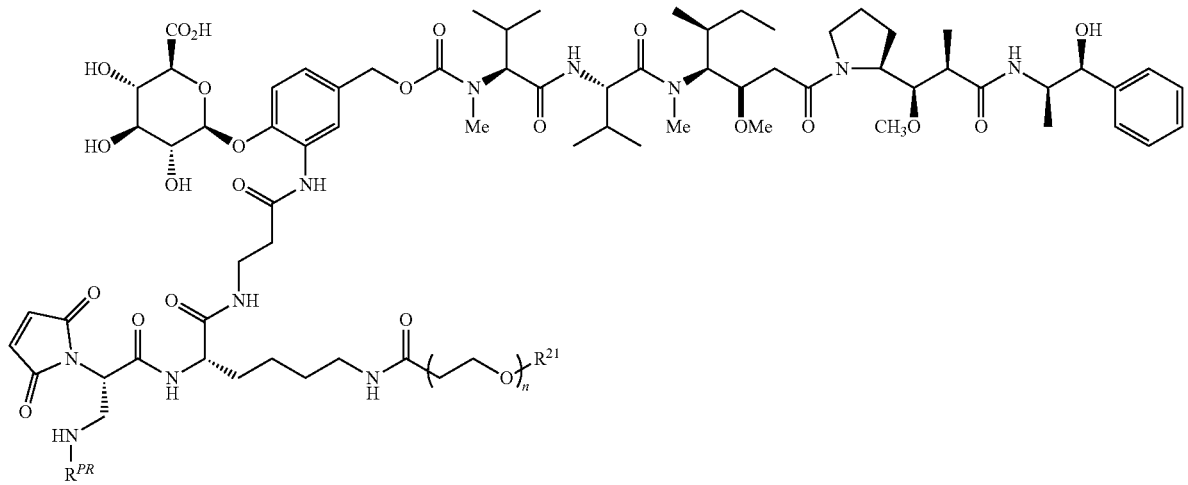

(VIa)

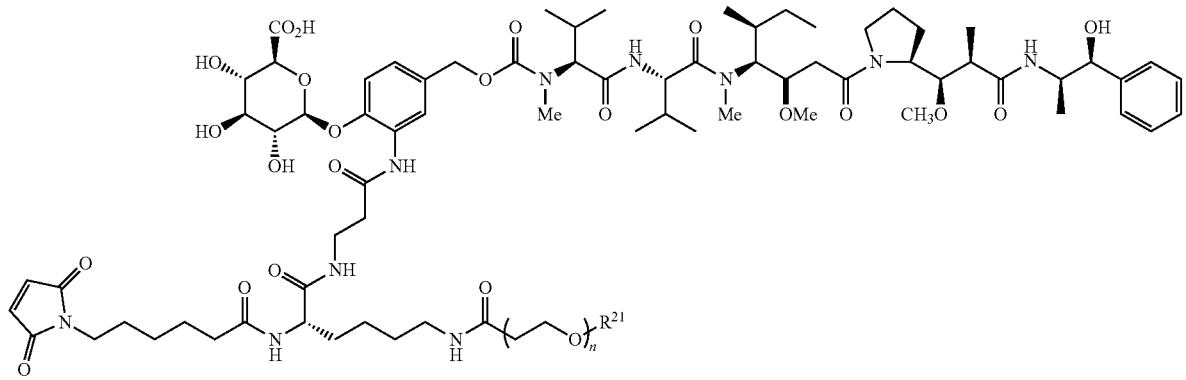

(VIIa)

or a pharmaceutically acceptable salt thereof wherein for formulas VI, VIa, VII and VIIa, n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —$CH_3$ or —$CH_2CH_2CO_2H$.

As noted above, $R^{PR}$ can be hydrogen or a protecting group. Protective groups as used herein refer to groups which selectively block, either temporarily or permanently, a reactive site in a multifunctional compound. A protecting group is a suitable protecting group when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. Suitable amine protecting groups include acid-labile nitrogen protecting groups, including those provided by Isidro-Llobel et al. "Amino acid-protecting groups" Chem. Rev. (2009) 109: 2455-2504. Typically, an acid-labile nitrogen-protecting group transforms a primary or secondary amino group to its corresponding carbamate and includes t-butyl, allyl, and benzyl carbamates.

As noted above, $R^{21}$ is a capping unit for the polyethylene glycol moiety. As will be appreciated by the skilled artisan, polyethylene glycol units can be terminally capped with a wide diversity of organic moieties, typically those that are relatively non-reactive. Alkyl and substituted alkyl groups are preferred, including, for example, —$C_{1-10}$ alkyl, —$C_{2-10}$ alkyl-$CO_2H$, —$C_{2-10}$ alkyl-OH, —$C_{2-10}$ alkyl-$NH_2$, $C_{2-10}$ alkyl-NH($C_{1-3}$ alkyl), or $C_{2-10}$ alkyl-N($C_{1-3}$ alkyl)$_2$.

Generally, for pegylated MMAE drug-linkers there are 1 to 16 drug-linkers attached to each antibody.

Drug Loading—"p"

Referring to the CD123 targeted antibody-drug conjugates of formulas II, IIa, and IIb, the subscript p represents the drug load for an antibody molecule (number of molecules of drug attached to an antibody molecule) and is an integer value. In a composition comprising a population of antibody-drug conjugate molecules, the average drug load (e.g., the average number of drug-linker molecules per antibody in the population) is an important quality attribute as it determines the amount of drug that can be delivered to a target cell. The average drug load can be an integer or non-integer value but is typically a non-integer value. The optimal average drug load will vary depending on the identity of the drug or drug-linker combination.

The heterogeneity of an antibody-drug conjugate composition will, in some aspects, be dependent on the conjugation technology used to conjugate drug-linker molecules to antibody molecules. For example, in some aspects, the conjugation technology used to conjugate the drug-linker molecules to the antibody molecules will result in an antibody-drug conjugate composition that is heterogenous with respect to the distribution of drug-linker molecules on the antibody and/or with respect to number of drug-linkers on the antibody molecules (e.g., when conjugating via interchain disulfides using non-site specific technology). In other aspects, the conjugation technology used to conjugate the drug-linker molecules will result in an antibody-drug conjugate composition that is substantially homogenous with respect to the distribution of drug-linker molecules on the ligand molecules and/or with respect to number of drug-linkers molecules on the antibody molecules (e.g., when using site specific conjugation technology). With both site specific and non-site specific methods, there will typically also be a small percentage of unconjugated antibody molecules. The percentage of unconjugated antibody molecules is included in the average drug load value.

In preferred aspects of the present invention, the average drug load when referring to a composition comprising a population of antibody-drug conjugate compounds is from about 2 to about 14, preferably about 2 to about 10. For PBD antibody drug conjugates, such as those exemplified herein, a particularly preferred average drug load is about 2. In some aspects, the actual drug load for individual antibody molecules in the population of antibody-drug conjugate compounds is from 1 to 4, 1 to 3 or 1 to 2 with a predominant drug loading of 2. In preferred aspects, the average drug load of about 2 is achieved via site specific conjugation techniques (e.g., engineered cysteines introduced to the antibody)

In some other aspects of the present invention, the average drug load when referring to a composition comprising a population of antibody-drug conjugate compounds is about 3 or about 4 and the actual drug load for individual antibody molecules in the population of antibody-drug conjugate compounds is from 1 to 8.

For the MMAE PEGylated ADCs, such as those exemplified herein, a particularly preferred average drug load is about 8. In exemplary embodiments, the drug-linkers are conjugated to the cysteine residues of the reduced interchain disulfides. In some aspects, the actual drug load for individual antibody molecules in the population of antibody-drug conjugate compounds is from 1 to 10 (or from 6 to 10 or from 6 to 8) with a predominant drug loading of 8. A higher drug load can be achieved, for example, if, in addition to the interchain disulfides, drug-linker is conjugated to introduced cysteine residues (such as a cysteine residue introduced at position 239, according to the EU index).

Exemplary ADCs include the following:

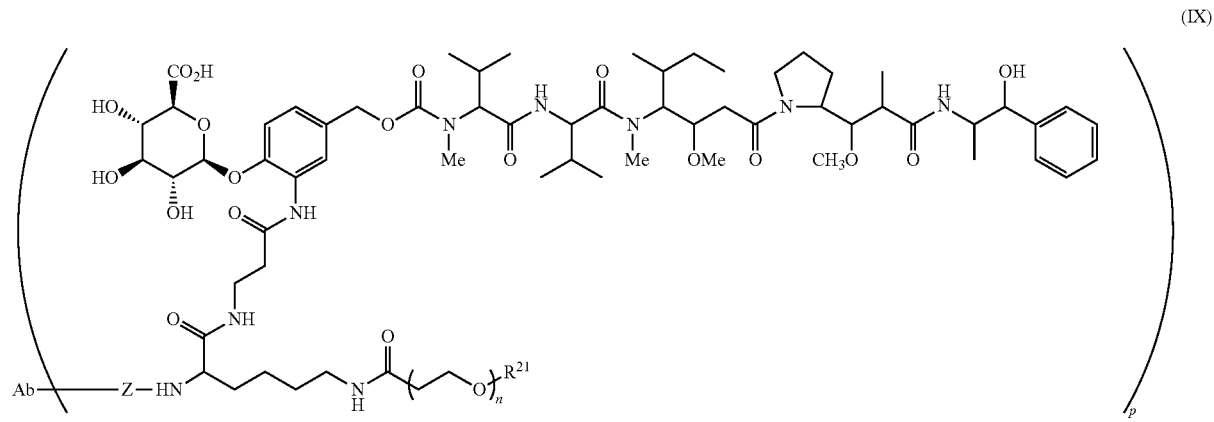

(IX)

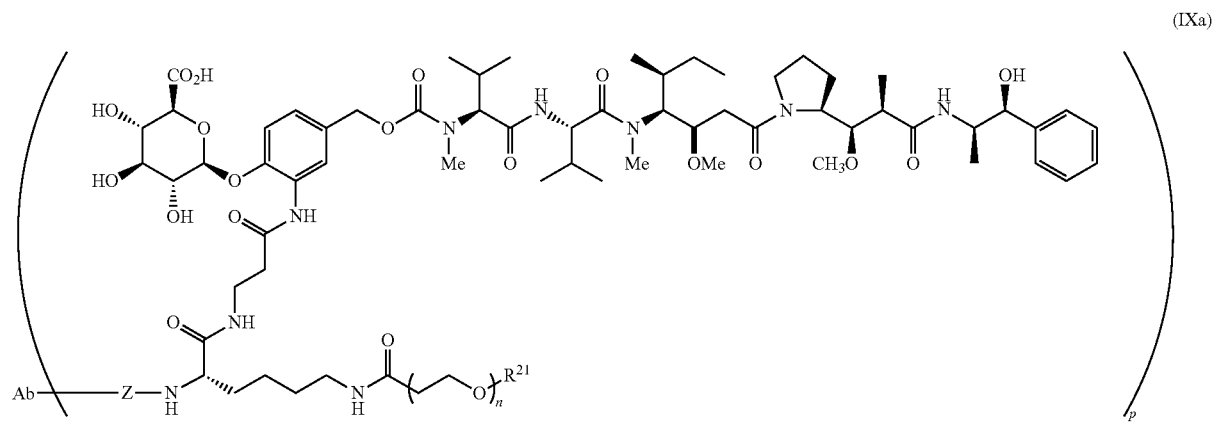

(IXa)

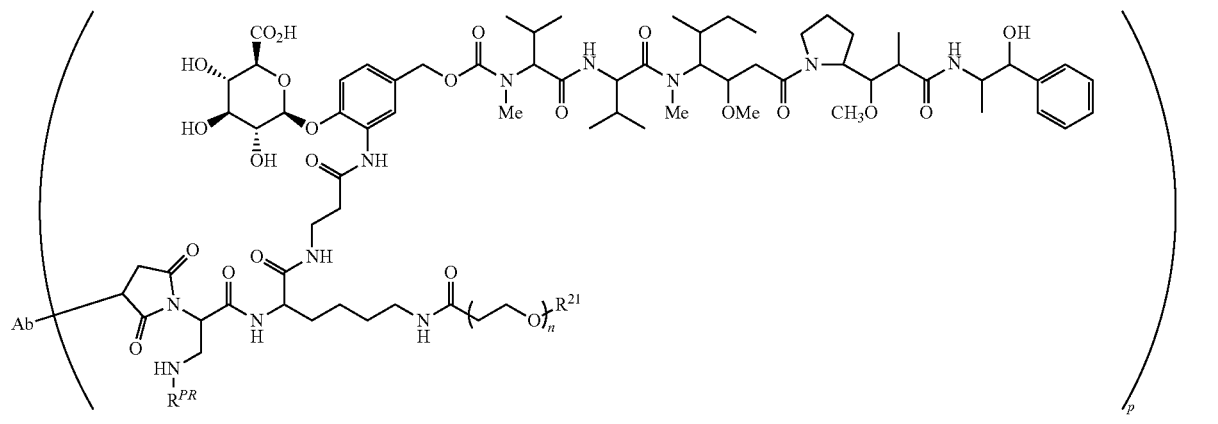
(X)
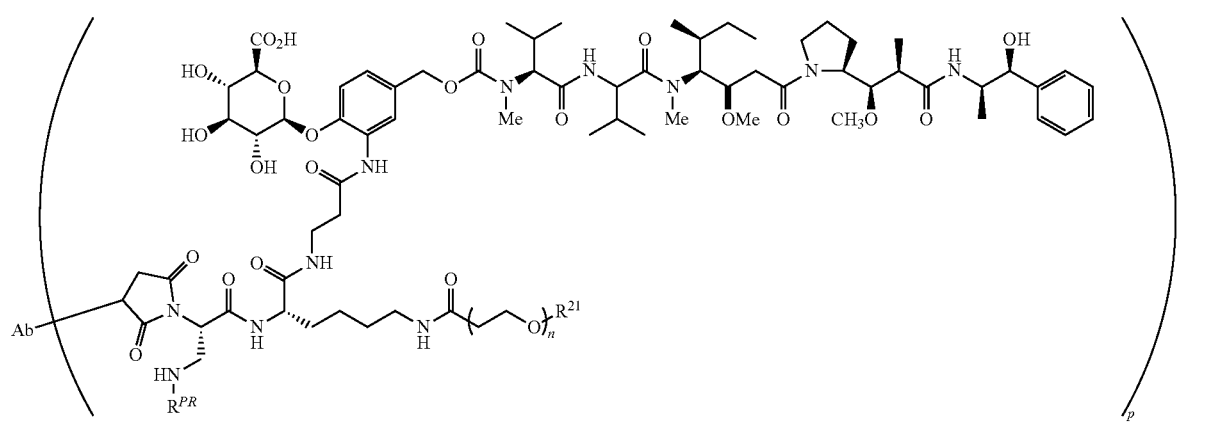
(Xa)
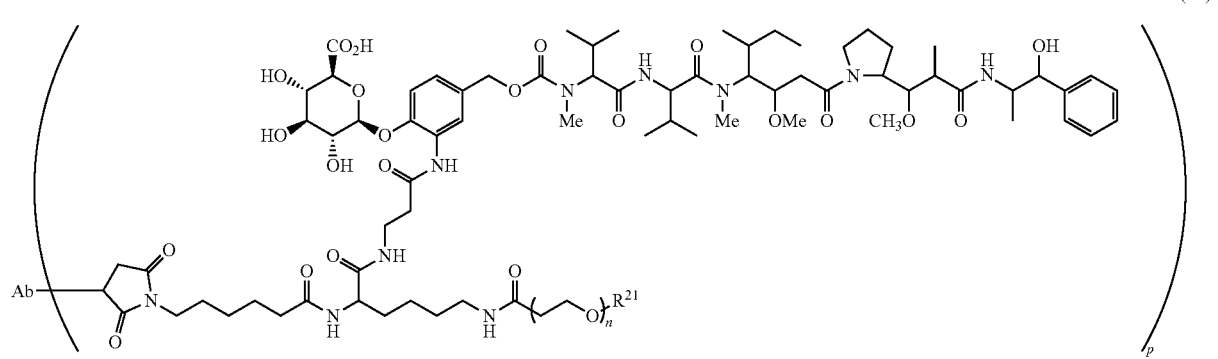
(XI)
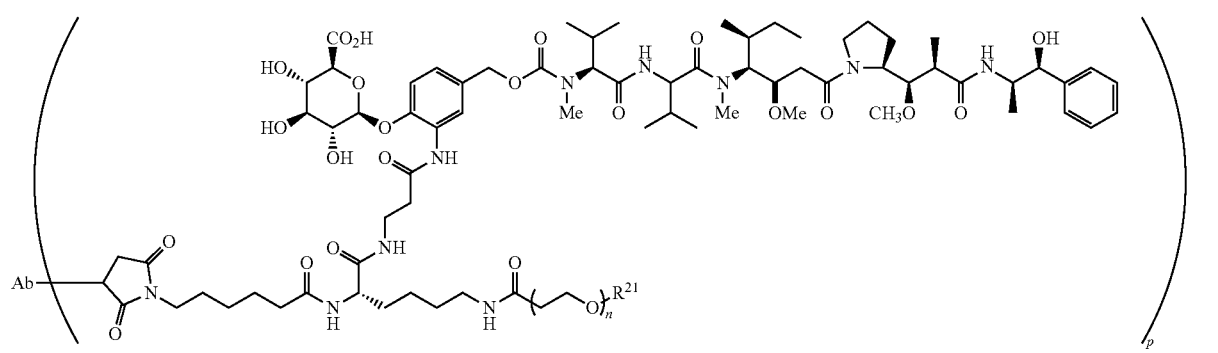
(XIa)

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably —$CH_3$ or —$CH_2CH_2CO_2H$, Ab represents an anti-CD48 antibody and p represents an integer ranging from 1 to 16, preferably 1 to 14, 6 to 12, 6 to 10, or 8 to 10 when referring to individual antibody molecules or to an average drug load of from about 4 or about 6 to about 14, preferably about 8 when referring to a population of antibody molecules.

As noted above, the PEG (polyethylene glycol) portion of the drug linker can range from 8 to 36, however, it has been found that a PEG of 12 ethylene oxide units is particularly preferably. It has been found that longer PEG chains can result in slower clearance whereas shorter PEG chains can result in diminished activity. Accordingly, the subscript n in all of the embodiments above is preferably 8 to 14, 8 to 12, 10 to 12 or 10 to 14 and is most preferably 12.

Polydisperse PEGS, monodisperse PEGS and discrete PEGs can be used to make the PEGylated antibody drug conjugates of the present invention. Polydisperse PEGs are a heterogeneous mixture of sizes and molecular weights whereas monodisperse PEGs are typically purified from heterogenous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length. As with the subscript "p", when referring to populations of antibody-drug conjugates, the value for the subscript "n" can be an average number and can be an integer or non-integer number.

In preferred embodiments, covalent attachment of the antibody to the drug-linker is accomplished through a sulfhydryl functional group of the antibody interacting with a maleimide functional group of a drug linker to form a thio-substituted succinimide. The sulfhydryl functional group can be present on the Ligand Unit in the Ligand's natural state, for example, in a naturally-occurring residue (inter-chain disulfide resides), or can be introduced into the Ligand via chemical modification or by biological engineering, or a combination of the two. It will be understood that an antibody-substituted succinimide may exist in hydrolyzed form(s). For example, in preferred embodiments, an ADC is comprised of a succinimide moiety that when bonded to the antibody is represented by the structure of

or is comprised of its corresponding acid-amide moiety that when bonded to the antibody is represented by the structure of:

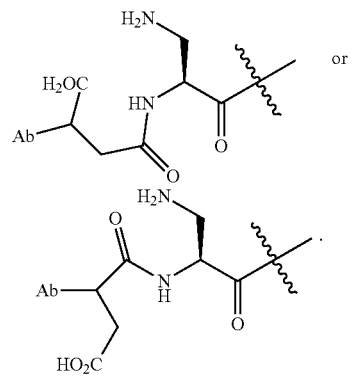

The wavy line indicates linkage to the remainder of the drug-linker.

The average number of Drug-Linker units per Ligand unit in a preparation from a conjugation reaction may be characterized by conventional means such as mass spectroscopy, ELISA assay, HIC and HPLC. The quantitative distribution of Ligand-Linker-Drug conjugates in terms of p may also be determined. In some instances, separation, purification, and characterization of homogeneous Ligand-Drug Conjugates, where p is a certain value from Ligand-Drug Conjugate with other drug loadings may be achieved by means such as reverse phase HPLC or electrophoresis.

VI. Therapeutic Applications

The CD123 targeted antibody-drug conjugates described herein can be used to treat a CD123 expressing disorder, such as CD123 expressing cancer. Typically such cancers show detectable levels of CD123 measured at the protein (e.g., by immunoassay) or RNA level. Some such cancers show elevated levels of CD123 relative to noncancerous tissue of the same type, preferably from the same patient. Optionally, a level of CD123 in a cancer is measured before performing treatment.

Examples of cancers associated with CD123 expression include myeloid diseases such as, acute myeloid leukemia (AML) and myelodysplastic syndrome (MDS). Other cancers include B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

Methods of the present invention include treating a patient that has a cancer that expresses CD123 comprising administering to the patient an antibody-drug conjugate of the present invention. The cancer can be any CD123 expressing cancer, including, for example, AML, MDS, B-ALL, hairy cell leukemia, Fanconi anemia, BPDCN, Hodgkin's disease, Immature T-ALL, Burkitt's lymphoma, Follicular lymphoma, CLL, or mantle cell lymphoma.

Some cancer cells develop resistance to a therapeutic agent after increasing expression of a protein increases efflux of the therapeutic agent out of the cancer cell. Such proteins include P-glycoprotein, multidrug resistance-associated protein, lung resistance-related protein, and breast cancer resistance protein. Detection of drug resistance in cancer cells can be performed by those of skill. Antibodies or assays that detect efflux proteins are commercially available from, e.g., Promega, Millipore, Abcam, and Sigma- Aldrich. The cancer to be treated by the present methods can be a multi-resistant cancer that expresses CD123. In some aspects, the cancer will be a multi-drug resistant CD123+ AML.

CD123 directed antibody-drug conjugates are administered in an effective regimen meaning a dosage, route of administration and frequency of administration that delays the onset, reduces the severity, inhibits further deterioration, and/or ameliorates at least one sign or symptom of cancer.

Exemplary dosages for CD123 directed conjugates include from about 1.0 μg/kg to about 10 mg/kg, 1.0 μg/kg to about 5 mg/kg, 1.0 μg/kg to about 5 mg/kg, from about 1.0 μg/kg to about 1.0 mg/kg, from about 10 μg/kg to about 3 mg/kg, from about 10 μg/kg to about 2 mg/kg, from about 1.0 μg/kg to 1.0 mg/kg, or from about 1.0 μg/kg to 500.0 μg/kg or from about 1.0 μg/kg to 80.0, 100.0, or 200.0 μg/kg.

Exemplary dosages for CD123 directed PBD conjugates are generally from about 1.0 μg/kg to 1.0 mg/kg, or from about 1.0 μg/kg to 500.0 μg/kg or from about 1.0 μg/kg to 80.0, 100.0, or 200.0 μg/kg, although alternate dosages are contemplated.

Administration can be by a variety of administration routes. In certain embodiments, the conjugates are administered parenterally, such as intravenously, intramuscularly, or subcutaneously. For administration of an ADC for the treatment of cancer, the delivery can be into the systemic circulation by intravenous or subcutaneous administration. In a particular embodiment, administration is via intravenous delivery. Intravenous administration can be, for example, by infusion over a period such as 30-90 minutes or by a single bolus injection. In some aspects, administration will be via slow IV push (i.e., over 30-60 seconds) in a peripherally inserted central catheter.

The frequency of administration depends upon many different factors, including means of administration, target site, physiological state of the patient, whether the patient is human or an animal, and other medications administered. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are every three weeks or between once weekly or once monthly over a continuous course of treatment, although more or less frequent dosing is also possible. For subcutaneous administration, an exemplary dosing frequency is daily to monthly, although more or less frequent dosing is also possible.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, conjugates can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of conjugate in a liquid formulation can vary widely. In some aspects, the ADC is present at a concentration from about 0.5 mg/ml to about 30 mg/ml, from about 0.5 mg/ml to about 10 mg/ml, from about 1 mg/ml to about 10 mg/ml, from about 2 mg/ml to about 10 mg/ml, or from about 2 mg/ml to about 5 mg/ml.

Treatment with conjugates of the invention can be combined with chemotherapy, radiation, stem cell treatment, surgery, and other treatments effective against the disorder being treated, including standard of care for the particular disorder being treated. Accordingly, the present invention encompasses methods of treating the disease and disorders described herein as a monotherapy or in combination therapy with, for example, standard of care or investigational drugs for treatment of such diseases and/or disorders. Methods for the treatment of cancer include administering to a patient in need thereof an effective amount of a CD123 directed antibody-drug conjugate of the present invention in combination with an additional anti-cancer agent or other agent to treat cancer.

One example of a combination therapy comprises a 7+3 regimen involving seven days of cytarabine and three days of an anthracycline such as (but not limited to) daunorubicin or idarubicin. In an embodiment, the 7+3 regimen of cytarabine and an anthracycline is administered in a combination therapy with a CD123 directed antibody-drug conjugate of the present invention. In a further embodiment, the 7+3 regimen of cytarabine and an anthracycline is administered in a combination therapy with a humanized 7G3 antibody-drug conjugate of the present invention. In a further embodiment, the 7+3 regimen of cytarabine and an anthracycline is administered in a combination therapy with an h7G3EC-SGD-1910 of the present invention. In some embodiments, the combination of a CD123 directed antibody-drug conjugate and a 7+3 regimen is applied to patients who are 60 years old or younger.

Another example of a combination therapy comprises a 7+3 regimen as described above plus cladribine. In an embodiment, the 7+3 regimen plus cladribine is administered in a combination therapy with a CD123 directed antibody-drug conjugate of the present invention. In a further embodiment, the 7+3 regimen plus cladribine is administered in a combination therapy with a humanized 7G3 antibody-drug conjugate of the present invention. In a further embodiment, the 7+3 regimen plus cladribine is administered in a combination therapy with an h7G3EC-SGD-1910 of the present invention.

Another example of a combination therapy comprises a hypomethylating agent such as (but not limited to) decitabine or azacitidine. In an embodiment, a hypomethylating agent is administered in a combination therapy with a CD123 directed antibody-drug conjugate of the present invention. In a further embodiment, a hypomethylating agent is administered in a combination therapy with a humanized 7G3 antibody-drug conjugate of the present invention. In a further embodiment, a hypomethylating agent is administered in a combination therapy with an h7G3EC-SGD-1910 of the present invention.

In some embodiments the combination of a CD123 directed antibody-drug conjugate and a hypomethylating agent is applied to patients who are treatment naïve, who are refractory to conventional treatments, or who have relapsed following a response to such treatments. In some embodiments the combination of a CD123 directed antibody-drug conjugate and a hypomethylating agent is used to treat elderly patients, e.g., patients 60 years old or older. Other frail or unfit patients can be treated using the combination of a CD123 directed antibody-drug conjugate and a hypomethylating agent, for example, patients that decline or who are not candidates for standard induction/consolidation treatment. Additionally, elderly patients with poor risk disease characteristics can also be treated using the combination, given the lack of benefit observed with intensive chemotherapy. Poor disease risk characteristics are known and described at, e.g., Hou et al., *Leukemia* 28:50-58 (2014).

Other agents and regimens for combination therapy include cytarabine, high-dose cytarabine, hydroxyurea, clofarabine, mitoxantrone, fludarabine, topotecan, etoposide, MEC (mitoxantrone, etoposide, and cytarabine), CLAG-M (cladribine, cytarabine, mitoxantrone, and filgrastim), and FLAG-IDA (fludarabine, cytarabine, idarubicin, and filgrastim). In an embodiment, one or more of hydroxyurea, clofarabine, mitoxantrone, fludarabine, topotecan, etoposide, MEC (mitomycin, etoposide, and cytarabine), CLAG-M (cladribine, cytarabine, mitoxantrone, and filgrastim), and FLAG-IDA (fludarabine, cytarabine, idarubicin, and filgrastim) is administered in a combination therapy with a CD123 directed antibody-drug conjugate of the present invention.

In a further embodiment, one or more of cytarabine, high-dose cytarabine, hydroxyurea, clofarabine, mitoxantrone, fludarabine, topotecan, etoposide, MEC (mitoxantrone, etoposide, and cytarabine), CLAG-M (cladribine, cytarabine, mitoxantrone, and filgrastim), and FLAG-IDA (fludarabine, cytarabine, idarubicin, and filgrastim) is administered in a combination therapy with a humanized 7G3 antibody-drug conjugate of the present invention.

In a further embodiment, one or more of cytarabine, high-dose cytarabine, hydroxyurea, clofarabine, mitoxantrone, fludarabine, topotecan, etoposide, MEC (mitoxantrone, etoposide, and cytarabine), CLAG-M (cladribine, cytarabine, mitoxantrone, and filgrastim), and FLAG-IDA (fludarabine, cytarabine, idarubicin, and filgrastim) is administered in a combination therapy with an h7G3EC-SGD-1910 of the present invention.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Methods
Competition Binding Assays

One hundred thousand CD123-positive cells were transferred to 96-well plates and incubated for 1 hour on ice with 5 nM AlexaFluor-488 labeled m7G3 and increasing concentrations (from 0.01 nM to 680 nM) of unlabeled hybrid, humanized or murine 7G3 mAb. Cells were centrifuged, washed 3 times with PBS, and resuspended in 125 µL of a PBS+1% BSA solution. Fluorescence was analyzed using a flow cytometer, and the percent of saturated fluorescent signal was used to determine percent labeled 7G3 mAb bound. The EC50 was extrapolated by fitting the data to a sigmoidal dose-response curve with variable slope.

Saturation Binding Assays

One hundred thousand CD123-positive cells (HEK-293F cells transfected to express human or cynomologus CD123) were transferred to 96-well plates. AlexaFluor-488 labeled CD123 mAb was added in concentrations ranging from 1250 nM to 13.5 pM and the cells incubated on ice for 30 minutes. Cells were pelleted by centrifugation, washed 3 times with a PBS+1% BSA solution, and resuspended in 125 µL of PBS+1% BSA. Fluorescence was analyzed using a flow cytometer, and the percent of saturated fluorescent signal was used to determine percent bound and to subsequently calculate apparent Kd.

In Vitro Cytotoxicity Assay

AML cell lines or primary AML cells were treated with antibody-drug conjugates (ADC) for 96 hours at 37° C. In some experiments, non-antigen binding ADC was included as negative controls. Cell viability for the cell lines was measured using CelltiterGlo (Promega Corporation, Madison, Wis.) according to the manufacturer's instructions. Cells were incubated for 25 minutes at room temperature with the CelltiterGlo reagents and luminescence was measured on an Envision plate reader (Perkin Elmer, Waltham, Mass.). For the primary AML cells, the viability of AML blasts was measured by flow cytometry using Annexin V and propidium iodide staining. Results are reported as IC50, the concentration of compound needed to yield a 50% reduction in viability compared to vehicle-treated cells (control=100%).

In Vivo Activity Study
Subcutaneous AML Models

SCID mice were inoculated subcutaneously with $5 \times 10^6$ THP-1 or $2 \times 10^6$ KG-1 AML tumor cells. Tumor growth was monitored with calipers and the mean tumor volume was calculated using the formula (0.5×[length×width]). When the mean tumor volume reached approximately 100 mm$^3$, mice (n=8/group) were untreated or dosed intraperitoneally with a single dose of CD123 ADC or non-binding control ADC. For the KG-1 model, mice were treated with human IVIg (single intraperitoneal injection of 10 mg/kg) approximately four hours prior to administration of the therapeutic to minimize interaction of the test ADC with Fc receptors on AML cells. Mice were euthanized when tumor volumes reached approximately 1000 mm$^3$. All animal procedures were performed under a protocol approved by the Institutional Animal Care and Use Committee in a facility accredited by the Association for Assessment and Accreditation of Laboratory Animal Care.

Production of Antibody Drug Conjugates

Antibody drug conjugates were prepared as described in WO2011/130613 using the anti-CD123 antibodies described herein. Preparation of cysteine mutants of IgG1 mAb is generally described in US20100158909. The drug-linker SGD-1910 was conjugated to the anti-CD123 antibody via a thiol group of a cysteine residue introduced at position 239 of the IgG1 chain of the antibody and the average drug load was about 2 drugs per antibody. Antibodies with cysteine at the 239 position carry the designation EC.

Results
Design and Testing of Humanized mAbs

Several humanized 7G3 antibodies were constructed using the hIGHv1-2.02/IGHJ1.01 heavy chain variable region human germline and the hIGKV4-1.01/IGHJ2.01 light chain variable region human germline as the human acceptor sequences. The antibodies differed in the selection of amino acid residues to be mutated back to the mouse antibody or mouse germline sequence. The antibody designated HCLA (heavy chain as set forth in SEQ ID NO:1 (vHC) and the light chain as set forth in SEQ ID NO:2 (vLA)) was selected as the lead humanized 7G3 antibody on the basis of its (i) binding characteristics, (ii) ability to deliver drug and (iii) number of back mutations as compared to the other variants.

Figure 5:
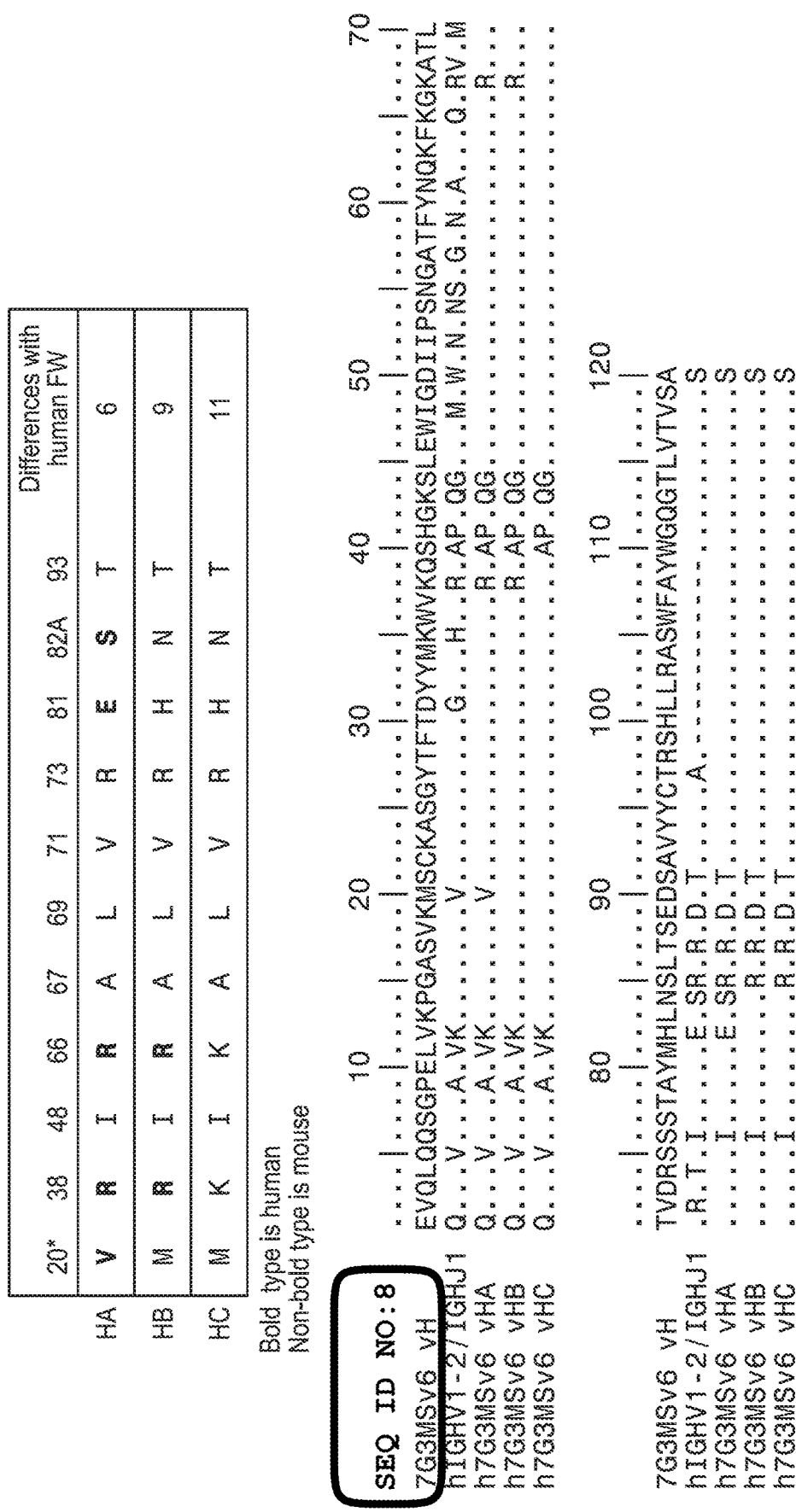
FIG. 5 shows the amino acid sequences for the heavy chain variable region of the murine 7G3 antibody and the humanized vHA, vHB, and vHC heavy chain and selected human germline acceptor variable region sequences.

Antibodies designated HALA (antibody having the heavy chain variable region designated vHA and the light chain variable region designated vLA), HALB (antibody having the heavy chain variable region designated vHA and the light chain variable region designated vLB), HBLA (antibody having the heavy chain variable region designated vHB and the light chain variable region designated vLA), HBLB (antibody having the heavy chain variable region designated vHB and the light chain variable region designated vLB), HCLB (antibody having the heavy chain variable region designated vHC and the light chain variable region designated vLB) can be used in the present invention in place of the HCLA antibody. See FIGS. 5 and 6 for the vHA, vHB, vHC, vLA, and vLB sequences. The binding affinities for the chimeric and various humanized forms of 7G3 are similar whether tested against a CD123-expressing AML cell line (Table 1) or HEK293 cells overexpressing human or cyno CD123 (Table 2).

TABLE 1

EC50 Binding Determinations for Humanized CD123 mAb Variants on Human CD123-Expressing Molm-13 AML Cells

| 7G3 Variant | Molm-13 EC50 (nM) |
| --- | --- |
| m7G3 | 4.3 |
| Chimeric 7G3 | 2.0 |
| HALA | 5.5 |
| HALB | 4.1 |
| HBLA | 2.8 |
| HBLB | 3.5 |
| HCLA | 2.6 |
| HCLB | 2.1 |

TABLE 2

Affinity Measurements of Humanized CD123 mAbs for Human and Cyno CD123-Expressing Cells

| 7G3 Variant | HEK293F-hCD123 | HEK293F-cyno CD123 |
| --- | --- | --- |
| m7G3 | 2.7 nM | 4.6 nM |
| chimeric 7G3 | 2.7 | 4.7 |
| h7G3, G1 | 2.7 | 5.3 |
| h7G3EC | 2.7 | 6.6 |

In Vitro Anti-Tumor Activity of h7G3EC-SGD-1910

Figure 2:
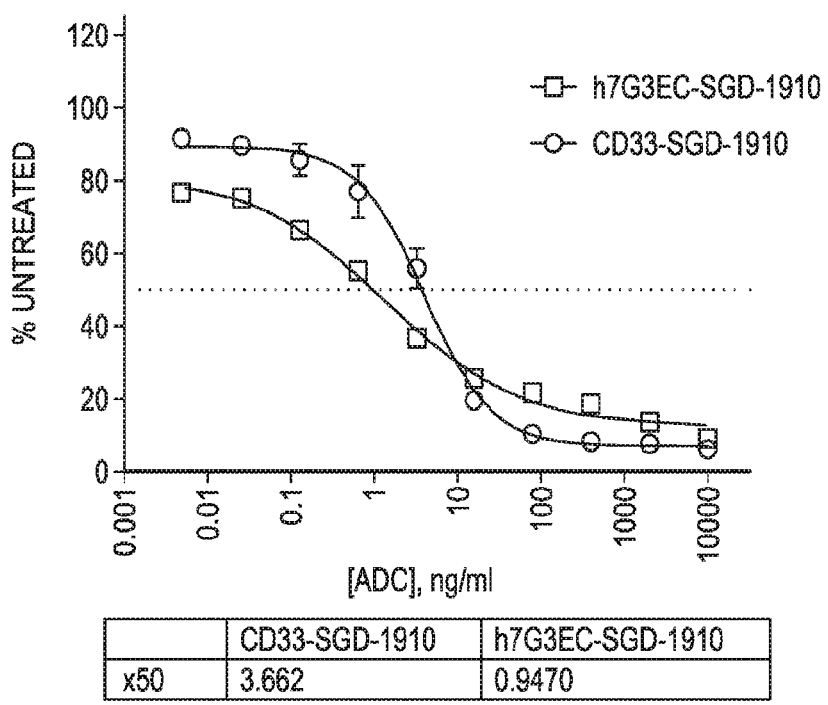
FIG. 2 shows the result of an in vitro cytotoxicity assay testing the humanized 7G3ec SGD-1910 antibody-drug conjugate against a MDR+-positive AML cell line, Kasumi-1, that expresses low copies of CD123 in comparison to CD33. Despite the low copy number, the h7G3ec SGD-1910 antibody-drug conjugate showed potent activity.

The cytotoxic activity of h7G3EC antibody conjugated to SGD-1910 (pyrrolobenzodiazapine dimer drug-linker) was evaluated against a panel of AML cell lines that expressed both CD123 and CD33. The activity was compared to that of an anti-CD33 antibody conjugated to SGD-1910 (CD33-SGD-1910). As shown in Table 3, the AML cell lines generally expressed lower copy numbers of CD123 as compared to CD33. The h7G3EC-SGD-1910 ADC was active against 10 of 11 CD123-positive AML cell lines (mean IC50 for responsive cell lines, 7 ng/mL with a range of 0.02 to 38 ng/ml), whereas CD33-SGD-1910 had potent activity against 12 of 12 AML cell lines tested (mean IC50, 26 ng/mL with a range of 0.04 to 181 ng/ml). FIGS. 1 and 2 depict the potent activity of h7G3EC-SGD-1910 against two MDR-positive AML cell lines that express low copies of CD123 in comparison to CD33. The KG1-INV cell line expresses 5000 copies of CD123 compared to 7300 copies of CD33. The Kasumi-1 cell line expresses 2000 copies of CD123 as compared to 16000 copies of CD33. No cytotoxic activity was observed with h7G3EC-SGD-1910 against the HEL9217 AML cell line which did not express CD123. Further, h7G3EC-SGD-1910 was found to be active against 15 of 17 primary samples isolated from AML patients (see Table 4, mean IC50 for responsive samples, 1 ng/mL with a range of 0.06 to 6.5 ng/ml). In comparison, the CD33-SGD-1910 was active against 10 of 17 primary AML samples (mean IC50 for responsive samples, 2 ng/mL with a range of 0.23 to 7.7 ng/ml). No activity was observed when a non-binding ADC was tested against the AML cell lines or the primary AML samples (IC50>1000 ng/ml). Altogether, these data demonstrate that h7G3EC-SGD-1910 selectively targeted CD123-expressing cells and displayed potent cytotoxic activity towards AML cell lines and primary AML patient samples regardless of MDR status.

TABLE 3

In vitro activities of h7G3EC-SGD-1910 and CD33-SGD-1910 drug conjugates against AML cell lines

| | CD123 | CD33 | | IC50, ng/ml | |
| --- | --- | --- | --- | --- | --- |
| Cell Line | Receptor Number | Receptor Number | MDR Status | h7G3EC-SGD-1910 | CD33-SGD-1910 |
| HNT-34 | 24400 | <20000 | − | 0.35 | 76 |
| Molm-13 | 20000 | 38000 | − | 0.08 | 0.25 |
| THP-1 | 8000 | 18000 | − | 24 | 5 |
| NOMO-1 | 7000 | 15000 | − | 38 | 12 |
| SKM-1 | 6600 | 24000 | − | 2.5 | 3.5 |
| MV4-11 | 26100 | 18500 | +/− | 0.02 | 0.04 |
| KG-1 | 9400 | 29000 | + | 0.8 | 1 |
| KG1-INV | 5000 | 7300 | + | 0.6 | 9 |
| GDM-1 | 5500 | 5900 | + | 3.5 | 181 |
| Kasumi-1 | 2000 | 16000 | + | 1 | 3.5 |
| TF1a | 2600 | 17000 | + | >1000 | 3 |
| HEL9217 | 0 | 19000 | + | >1000 | 17 |

MDR, multi-drug resistance;
+, dye efflux >2-fold above background

TABLE 4

In vitro activities of h7G3EC-1910 and CD33-SGD-1910 drug conjugates against primary AML samples

| | | | | IC50 (ng/mL) | |
| --- | --- | --- | --- | --- | --- |
| Sample Designation | CD123 Expression (MFI) | CD33 Expression (MFI) | MDR Status | h7G3EC-SGD-1910 | CD33-SGD-1910 |
| FH037 | 483 | 1593 | + | 0.68 | >2.5 |
| FH016 | 596 | 137 | + | 1.4 | >2.5 |
| FH025 | 1190 | 2527 | + | 6.5 | 7.7 |
| FH034 | 1204 | 4125 | + | 0.22 | 1 |
| FH023 | 2277 | 4987 | No data | 0.06 | 0.23 |
| FH038 | 2947 | 4031 | + | 0.18 | 1.3 |
| FH018 | 3142 | 2435 | + | 0.12 | 0.34 |
| FH036 | 3262 | 5068 | + | 0.16 | 0.31 |
| FH026 | 4599 | 3999 | + | 0.22 | 0.39 |
| FH028 | 828 | 549 | − | 2 | >2.5 |
| FH019 | 1480 | 472 | − | >2.5 | >2.5 |
| FH022 | 1485 | 257 | No data | 0.56 | >2.5 |
| FH020 | 1517 | 1603 | + | 2.5 | 2.8 |
| FH027 | 418 | 2841 | − | >2.5 | >2.5 |
| FH021 | 1558 | 99 | + | 1.6 | >2.5 |
| FH029 | 1824 | 1356 | + | 0.46 | 3 |
| FH024 | 2403 | 897 | + | 2 | 3 |

MFI, mean fluorescence intensity
MDR, multi-drug resistance;
+, dye efflux >2-fold above background In Vivo Anti-Tumor Activity of h7G3EC-SGD-1910

Figure 3:
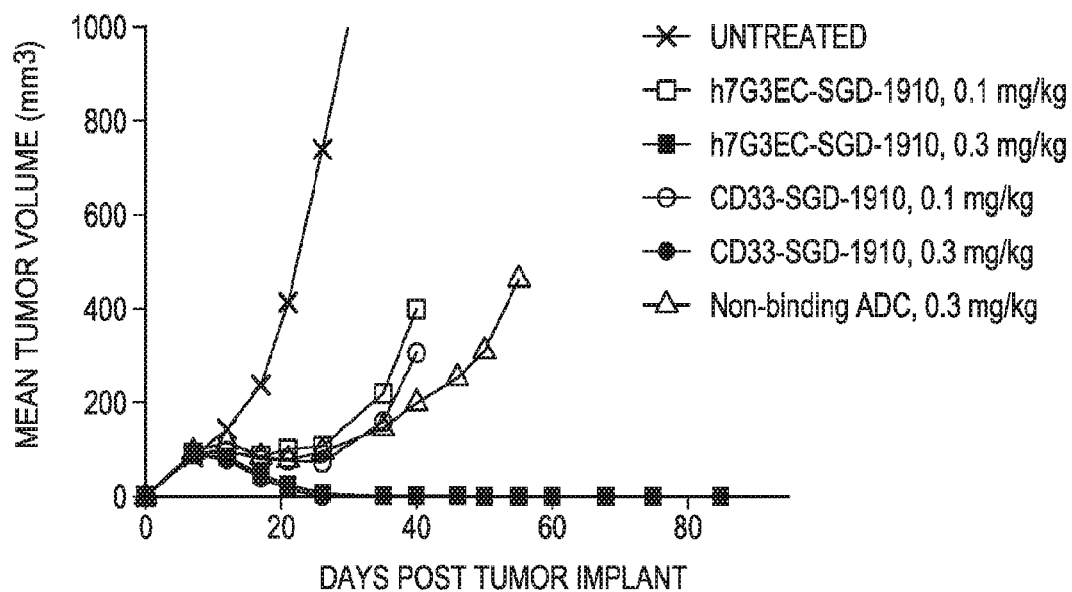
FIG. 3 shows the results of a AML xenograft model, THP-1, showing that the humanized 7G3ec SGD-1910 antibody-drug conjugate displayed potent activity despite low copy number. Activity was comparable to CD33 antibody-drug conjugates despite lower copy number.
Figure 4:
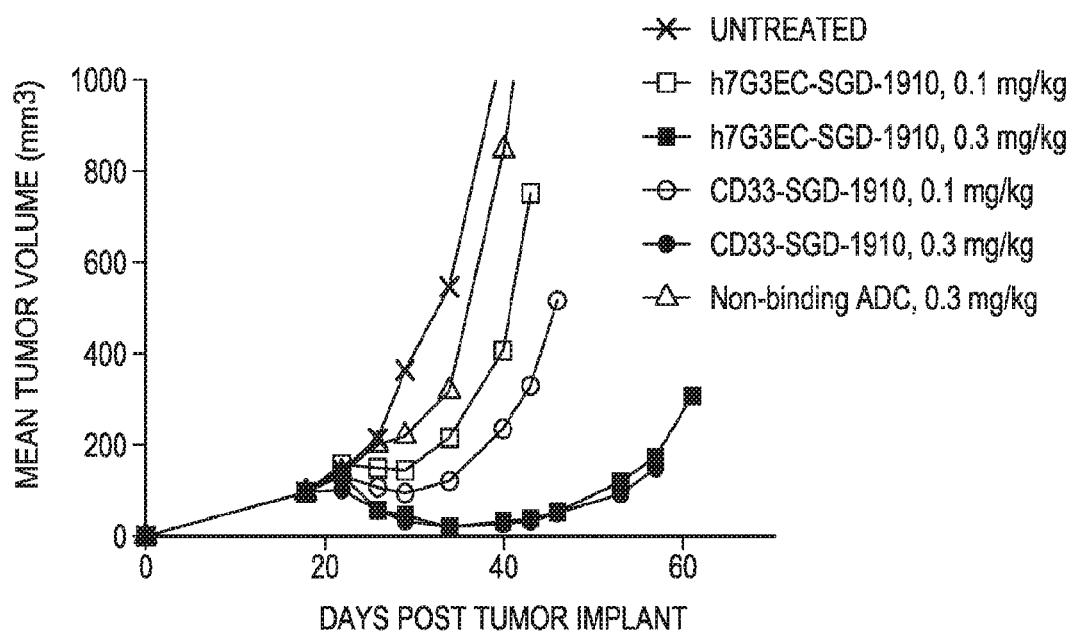
FIG. 4 shows the results of a AML xenograft model, KG1-INV, showing that the humanized 7G3ec SGD-1910 antibody-drug conjugate displayed potent activity and activity comparable to a CD33 antibody-drug conjugate despite lower copy number.

The activity of h7G3EC-SGD-1910 was tested in two subcutaneous AML xenograft models, THP-1 and KG-1. SCID mice bearing established (~100 mm$^3$) tumors were dosed with h7G3EC-SGD-1910 or non-binding control ADC (h00EC-SGD-1910) as depicted in FIG. 3 for the MDR-negative THP-1 model (8000 copies of CD123; 18000 copies of CD33) and in FIG. 4 for the MDR-positive KG-1 tumor model (7000 copies of CD123, 20000 copies of CD33). Treatment with h7G3EC-SGD-1910 significantly decreased tumor growth compared to untreated and non-binding control ADC-treated mice (p<0.0001). The anti-tumor activity observed with CD123-targeted ADC was dose dependent. For THP-1 tumors, a single dose of 0.1 mg/kg resulted in complete and durable tumor regression in 2 of 8 treated mice (FIG. 3). A higher dose of 0.3 mg/kg resulted in complete and durable regression in 8 of 8 treated mice, and the median day to tumor quadrupling had not been reached by the end of the study on day 85. In the MDR-positive KG-1 tumor model (FIG. 4), a single dose of 0.1 mg/kg h7G3EC-SGD-1910 resulted in complete and durable tumor regression in 1 of 8 treated mice. On the other hand, a single dose of 0.3 mg/kg yielded 1 complete regression and 3 complete and durable tumor regressions of 8 treated mice (p<0.008 compared to untreated mice). In contrast, the tumors in mice similarly dosed with the non-binding control ADC (h00EC-SGD-1910) had quadrupled in volume by day 35 and was not significantly different from the untreated mice. The anti-tumor responses of mice dosed with 0.1 mg/kg or 0.3 mg/kg CD33-SGD-1910 was similar to that of h7G3EC-SGD-1910 (FIG. 4). The data demonstrate that h7G3EC-SGD-1910 shows significant dose-dependent anti-tumor activity in AML xenograft models that express lower CD123 antigen levels compared to CD33.

Additional In Vivo AML Models
Methods
Subcutaneous AML Model

SCID mice were inoculated subcutaneously with $5 \times 10^6$ HNT-34 AML tumor cells. Tumor growth was monitored with calipers and the mean tumor volume was calculated using the formula (0.5×[length×width]). When the mean tumor volume reached approximately 100 mm$^3$, mice (n=8/group) were untreated or dosed intraperitoneally with a single dose of CD123 ADC or non-binding control ADC. Mice were euthanized when tumor volumes reached approximately 1000 mm$^3$. All animal procedures were performed under a protocol approved by the Institutional Animal Care and Use Committee in a facility accredited by the Association for Assessment and Accreditation of Laboratory Animal Care.

Disseminated AML Models

For the Molm-13 model, $5 \times 10^6$ cells were injected into the lateral tail vein of SCID mice and were untreated or dosed intraperitoneally with a single dose of CD123 ADC or non-binding control ADC 7 days later. Mice were treated with human IVIg (single intraperitoneal injection of 10 mg/kg) approximately four hours prior to administration of the therapeutic to minimize interaction of the test ADC with Fc receptors on AML cells. Animals were observed and euthanized for evidence of progressive disease such as hind limb paralysis or more than 15% weight loss. For the primary AML xenograft model, NOD/SCID/IL-2Rγnull mice (NSG; The Jackson Laboratory, Bar Harbor, Me.) were irradiated with 1 Gy one day before intravenous injection of $7 \times 10^5$ primary leukemia cells from a patient with relapsed AML (06227; AllCells, Emeryville, Calif.). Disease burden in the blood and bone marrow was monitored periodically by flow cytometric staining of human CD45+/CD33+ cells, and treatment was initiated when tumor burden approached 65%. To monitor treatment effects, small amounts of bone marrow were obtained from the femoral notch region between the epicondyles from mice under anesthesia and analyzed by flow cytometry. Data were plotted and analyzed using GraphPad Prism.

Results

Figure 7:
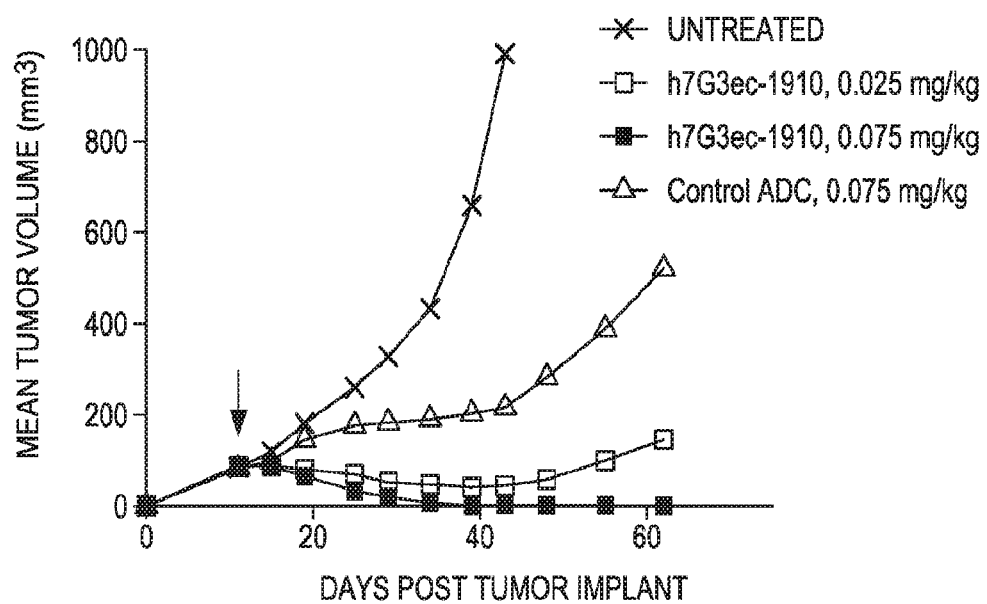
FIG. 7 shows the results of a AML xenograft model, HNT-34, showing that the humanized 7G3ec SGD-1910 antibody-drug conjugate displayed potent cytotoxic activity.

The activity of h7G3EC-SGD-1910 was further tested in one subcutaneous AML xenograft model, HNT-34, and two disseminated AML models, Molm-13 and a primary AML model. SCID mice bearing established (~100 mm$^3$) MDR-negative HNT-34 tumors (CD123 copy number ~24,000) were dosed with h7G3EC-SGD-1910 or non-binding control ADC as depicted in FIG. 7. Treatment with h7G3EC-SGD-1910 significantly decreased tumor growth compared to untreated and non-binding control ADC-treated mice (p<0.0001). The anti-tumor activity observed with the CD123-targeted ADC was dose dependent. A single dose of 0.025 mg/kg resulted in complete and durable tumor regression in 2 of 8 treated mice (FIG. 7). A higher dose of 0.075 mg/kg resulted in complete and durable regression in 7 of 8 treated mice. The median day to tumor quadrupling for the CD123-ADC groups had not been reached by the end of the study on day 62.

Figure 8:
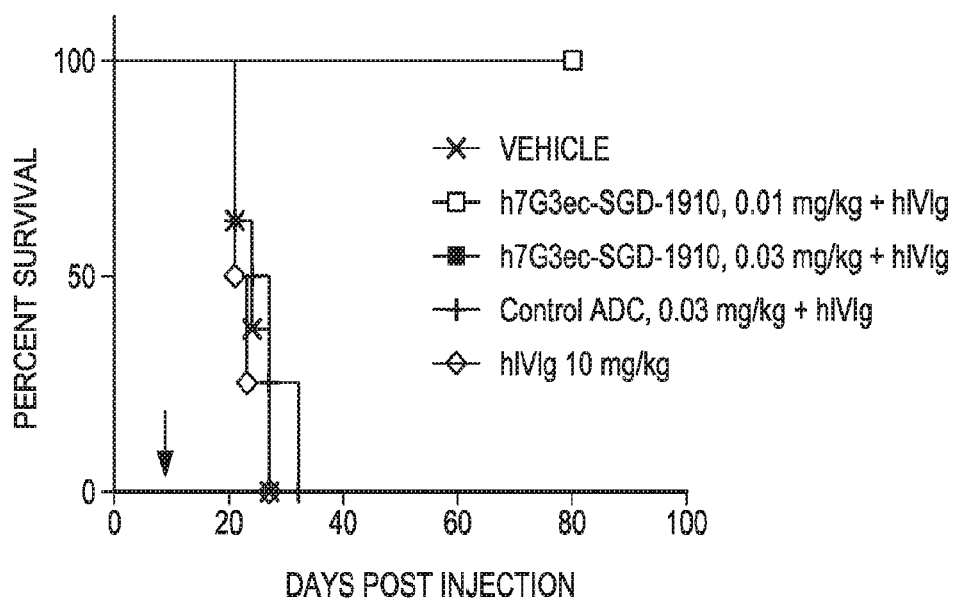
FIG. 8 shows shows the results of a AML xenograft model, the disseminated Molm-13 AML model, showing that the humanized 7G3ec SGD-1910 antibody-drug conjugate displayed potent cytotoxic activity.
Figure 9:
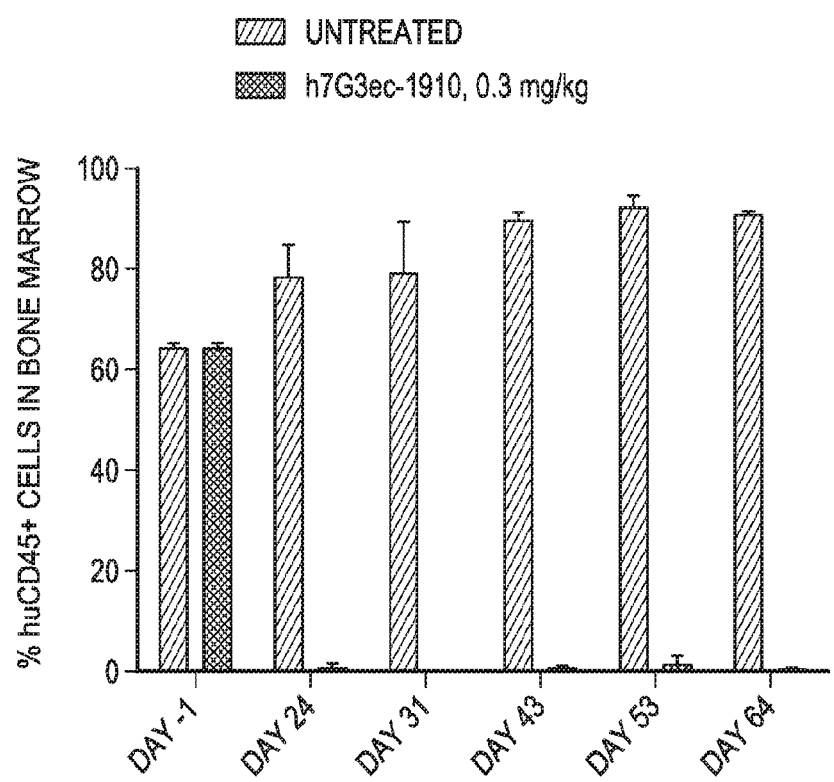
FIG. 9 shows the results of a AML xenograft model, a disseminated model of primary MDR+ AML, showing that the humanized 7G3ec SGD-1910 antibody-drug conjugate displayed potent cytotoxic activity.

In the MDR-negative Molm-13 disseminated model of AML (FIG. 8, CD123 copy number ~20,000), a single dose of 0.01 mg/kg or 0.03 mg/kg h7G3EC-SGD-1910 administered on Day 7 significantly improved the survival of the mice. The survival of the CD123-ADC treated mice was greater than 80 days compared to 22 to 25 days for the control groups (p<0.0001 compared to Untreated, hIVIg, or nonbinding Control ADC). The anti-leukemic response of CD123-ADC was also demonstrated in a xenograft model using primary leukemia cells (MDR+) from a patient with relapsed AML. The primary human leukemia cells were transplanted into NSG mice and allowed to grow to a 65% tumor burden in the bone marrow (CD123 copy number ~2200). The mice were dosed with 0.3 mg/kg CD123-SGD-1910 on Day 0 and Day 11 (FIG. 9). The tumor burden in the treated mice was significantly reduced by day 24 and remained at a reduced level until the end of the study at day 64.

The data demonstrate that h7G3EC-SGD-1910 has significant dose-dependent anti-tumor activity in several AML xenograft models, including models utilizing primary tumor cells from human patients with AML, that express different CD123 antigen levels and irrespective of MDR status.

| Informal Sequence listing |
|---|
| SEQ ID NO: 1, Heavy chain variable region for HC<br>QVQLVQSGAEVKKPGASVKMSCKASGYTFT<u>DYYMK</u>WVKQAPGQGLEWIG<u>D</u><br><u>IIPSNGATFYNQKFKG</u>KATLTVDRSISTAYMHLNRLRSDDTAVYYCTR<u>SH</u><br><u>LLRASWFAYW</u>GQGTLVTVSS |
| SEQ ID NO: 2, Light chain variable region for LA<br>DFVMTQSPDSLAVSLGERATINC<u>KSSQSLLNSGNQKNYL</u>TWYLQKPGQPP<br>KLLI<u>YWASTRESG</u>VPDRFSGSGSGTDFTLTISSLQAEDVAVYYC<u>QNDYSY</u><br><u>PYT</u>FGQGTKLEIKR |
| SEQ ID NO: 3, Heavy chain for HC with mutant IgG1<br>having a cysteine substitution at position 239,<br>according to the EU index as set forth in Kabat<br>QVQLVQSGAEVKKPGASVKMSCKASGYTFT<u>DYYMK</u>WVKQAPGQGLEWIG<u>D</u><br><u>IIPSNGATFYNQKFKG</u>KATLTVDRSISTAYMHLNRLRSDDTAVYYCTR<u>SH</u><br><u>LLRASWFAYW</u>GQGTLVTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPCVFLFPPKP<br>KDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |

Informal Sequence listing

SEQ ID NO: 4, Light chain for LA
DFVMTQSPDSLAVSLGERATINCKSSQSLLNSGNQKNYLTWYLQKPGQPP
KLLIYWASTRESGVPDRFSGSGSGTDFTLTISSLQAEDVAVYYCQNDYSY
PYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC SEQ ID NO: 5, mutant heavy chain constant region
(having a cysteine substitution at position 239,
according to the EU index as set forth in kabat)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPCVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPG SEQ ID NO: 6, Naturally occurring heavy chain
constant region
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPG SEQ ID NO: 7, Light chain constant region
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVIKS
FNRGEC SEQ ID NO: 8, murine 7G3 antibody heavy chain
variable region
EVQLQQSGPELVKPGASVKMSCKASGYTFTDYYMKWVKQSHGKSLEWIGD
IIPSNGATFYNQKFKGKATLTVDRSSSTAYMHLNSLTSEDSAVYYCTRSH
LLRASWFAYWGQGTLVTVSA SEQ ID NO: 9, murine 7G3 antibody light chain
variable region
DFVMTQSPSSLTVTAGEKVTMSCKSSQSLLNSGNQKNYLTWYLQKPGQPP
KLLIYWASTRESGVPDRFTGSGSGTDFTLTISSVQAEDLAVYYCQNDYSY
PYTFGGGTKLEIKR SEQ ID NO: 10-amino acid sequence of CDR-H1 of
humanized 7G3
DYYMK SEQ ID NO: 11-amino acid sequence of CDR-H2 of
humanized 7G3
DIIPSNGATFYNQKFKG SEQ ID NO: 12-amino acid sequence of CDR-H3 of
humanized 7G3
SHLLRASWFAY SEQ ID NO: 13-amino acid sequence of CDR-L1 of
humanized 7G3
KSSQSLLNSGNQKNYLT SEQ ID NO: 14-amino acid sequence of CDR-L2 of
humanized 7G3
WASTRES SEQ ID NO: 15-amino acid sequence of CDR-L3 of
humanized 7G3
QNDYSYPYT

What is claimed is:

1. An anti-CD123 antibody-drug conjugate compound having the formula:

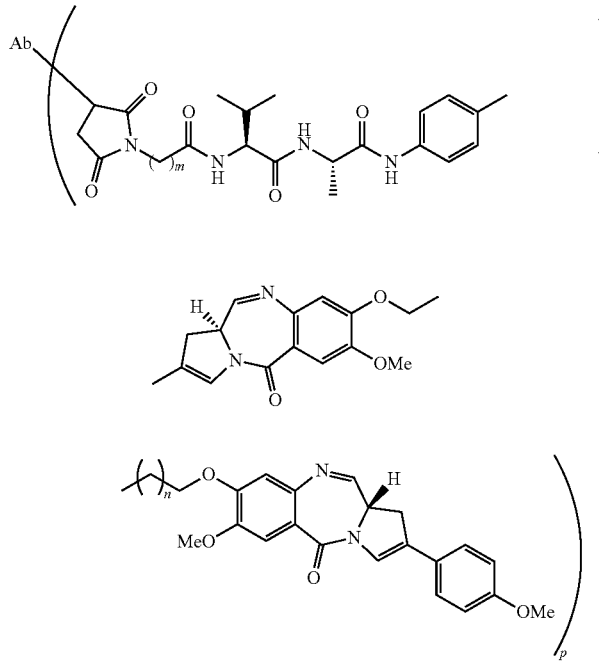

or a pharmaceutically acceptable salt thereof; wherein
the subscript n is 1 or 3;
the subscript m is 2 to 5
Ab is an anti-CD123 intact antibody or antigen binding fragment thereof comprising a heavy chain variable region having the amino acid sequence set forth in SEQ ID NO:1;
and a light chain variable region having the amino acid sequence set forth in SEQ ID NO:2;
the subscript p is an integer from 1 to 4.

2. The compound of claim 1 wherein n is 1.

3. The compound of claim 1 wherein n is 3.

4. The compound of claim 1 wherein m is 5.

5. The compound of claim 1 wherein attachment to Ab is via a sulfur atom of an engineered cysteine residue of Ab.

6. The compound of claim 1 wherein Ab comprises a heavy chain variable region having the amino acid sequence set forth in SEQ ID NO:1 fused to a human heavy chain constant region; and a light chain variable region having the amino acid sequence set forth in SEQ ID NO:2 fused to a human light chain constant region.

7. The compound of claim 6 wherein Ab comprises a heavy chain having the amino acid sequence set forth in SEQ ID NO:3 and a light chain having the amino acid sequence set forth in SEQ ID NO:4 and attachment to Ab is via a sulfur atom or an engineered cysteine residue at position 239 of the heavy chain constant region, according to the EU index system of numbering.

8. The compound of claim 1 wherein p is 2.

9. A pharmaceutical composition comprising a population of anti-CD123 antibody-drug conjugate molecules having the formula:

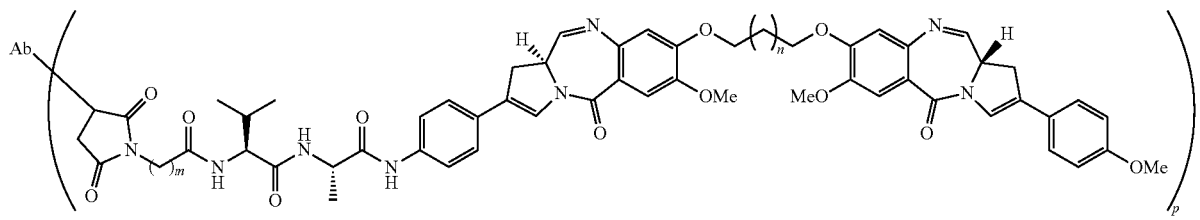

or a pharmaceutically acceptable salt thereof; wherein
the subscript n is 1 to 3;
the subscript m is 2 to 5
Ab is an anti-CD123 intact antibody or antigen binding fragment thereof comprising a heavy chain variable region having the amino acid sequence set forth in SEQ ID NO:1;
and a light chain variable region having the amino acid sequence set forth in SEQ ID NO:2;
the subscript p is an integer from 1 to 4; and the average drug load of the composition is about 2.

10. The pharmaceutical compositions of claim 9 wherein n is 1.

11. The pharmaceutical compositions of claim 9 wherein n is 3.

12. The pharmaceutical composition of claim 9 wherein m is 5.

13. The pharmaceutical composition of claim 9 wherein attachment to Ab is via a sulfur atom of an engineered cysteine residue of Ab.

14. The pharmaceutical composition of claim 9 wherein Ab comprises a heavy chain variable region having the amino acid sequence set forth in SEQ ID NO:1 fused to a human heavy chain constant region; and a light chain variable region having the amino acid sequence set forth in SEQ ID NO:2 fused to a human light chain constant region.

15. The pharmaceutical composition of claim 14 wherein Ab comprises a heavy chain having the amino acid sequence set forth in SEQ ID NO:3 and a light chain having the amino acid sequence set forth in SEQ ID NO:4 and attachment to Ab is via a sulfur atom or an engineered cysteine residue at position 239 of the heavy chain constant region, according to the EU index system of numbering.

16. The pharmaceutical composition claim 9 of wherein p is 1 or 2.

17. The pharmaceutical composition claim 9 of in aqueous form.

18. The pharmaceutical composition of claim 9 in lyophilized form.

19. A method of treating a patient having a cancer that expresses CD123, comprising administering to the patient an effective regimen of a pharmaceutical composition of claim 9.

20. The method of claim 19 wherein the cancer is acute myeloid leukemia (AML).

21. The method of claim 19 wherein the cancer is myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

22. An antibody-drug conjugate composition comprising a population of anti-CD123 antibody-drug conjugate molecules having the formula:

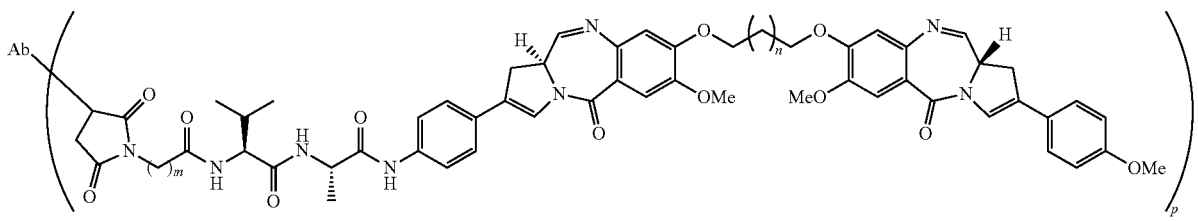

or a pharmaceutically acceptable salt thereof; wherein
the subscript n is 1 to 3;
the subscript m is 2 to 5
Ab is an anti-CD123 intact antibody or antigen binding fragment thereof comprising a heavy chain variable region having the amino acid sequence set forth in SEQ ID NO:1;
and a light chain variable region having the amino acid sequence set forth in SEQ ID NO:2; and
the subscript p is an integer from 1 to 4; and the average drug load of the composition is about 2.

23. The compositions of claim 19 wherein n is 1.

24. The compositions of claim 19 wherein n is 3.

25. The composition of claim 19 wherein m is 5.

26. The composition of claim 19 wherein attachment to Ab is via a sulfur atom of an engineered cysteine residue of Ab.

27. The composition of claim 19 wherein Ab comprises a heavy chain variable region having the amino acid sequence set forth in SEQ ID NO:1 fused to a human heavy chain constant region; and a light chain variable region having the amino acid sequence set forth in SEQ ID NO:2 fused to a human light chain constant region.

28. The composition of claim 27 wherein Ab comprising a heavy chain having the amino acid sequence set forth in SEQ ID NO:3 and a light chain having the amino acid sequence set forth in SEQ ID NO:4 and attachment to Ab is via a sulfur atom or an engineered cysteine residue at position 239 of the heavy chain constant region, according to the EU index system of numbering.

29. A pharmaceutical composition comprising a population of anti-CD123 antibody-drug conjugate molecules having the formula:

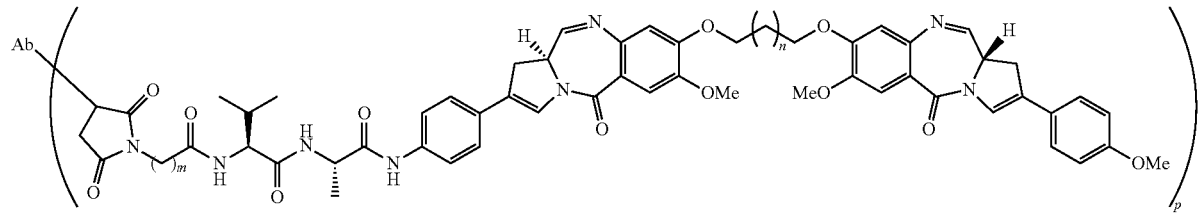

or a pharmaceutically acceptable salt thereof; wherein
the subscript n is 1 to 3;
the subscript m is 2 to 5
Ab is an anti-CD123 intact antibody or antigen binding fragment thereof comprising a heavy chain variable region having the amino acid sequence set forth in SEQ ID NO:3; and a light chain variable region having the amino acid sequence set forth in SEQ ID NO:4 and attachment to Ab is via a sulfur atom or an engineered cysteine residue at position 239 of the heavy chain constant region, according to the EU index system of numbering;
the subscript p is 1 or 2;
and the average drug load of the composition is about 2.

30. A method of treating a patient having a cancer that expresses CD123, comprising administering to the patient an effective regimen of a pharmaceutical composition comprising a population of anti-CD123 antibody-drug conjugate molecules having the formula:

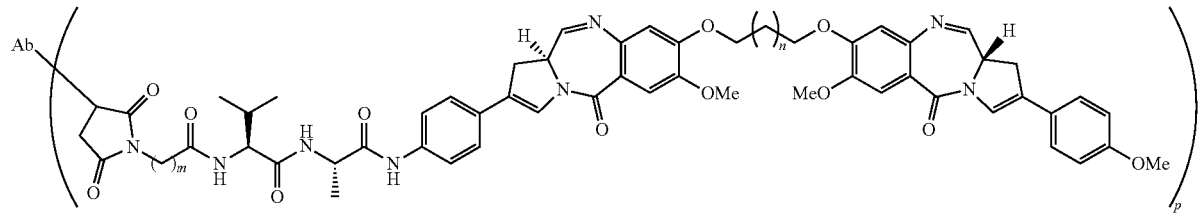

or a pharmaceutically acceptable salt thereof; wherein
the subscript n is 1 to 3;
the subscript m is 2 to 5
Ab is an anti-CD123 intact antibody or antigen binding fragment thereof comprising a heavy chain variable region having the amino acid sequence set forth in SEQ ID NO:1;
and a light chain variable region having the amino acid sequence set forth in SEQ ID NO:2;
the subscript p is an integer from 1 to 4; and the average drug load of the composition is about 2.

31. The method of claim 30 wherein the cancer is acute myeloid leukemia (AML).

32. The method of claim 30 wherein the cancer is myelodysplastic syndrome (MDS), B-cell acute lymphoblastic leukemia (B-ALL), hairy cell leukemia, Fanconi anemia, Blastic plasmacytoid dendritic cell neoplasm (BPDCN), Hodgkin's disease, Immature T-cell acute lymphoblastic leukemia (Immature T-ALL), Burkitt's lymphoma, Follicular lymphoma, chronic lymphocytic leukemia (CLL), or mantle cell lymphoma.

33. An anti-CD123 intact antibody or antigen binding fragment thereof comprising a heavy chain variable region having the amino acid sequence set forth in SEQ ID NO:1; and a light chain variable region having the amino acid sequence set forth in SEQ ID NO:2.

34. The antibody of claim 33 wherein the heavy chain variable region is fused to a heavy chain constant region; and the light chain variable region is fused to a light chain constant region.

35. The antibody of claim 33 comprising a heavy chain having the amino acid sequence set forth in SEQ ID NO:3 and a light chain having the amino acid sequence set forth in SEQ ID NO:4.

36. The intact antibody or antigen binding fragment of claim 33 conjugated to a cytotoxic agent.

37. The intact antibody or antigen binding fragment of claim 36 wherein the cytotoxic agent is a maytansinoid, auristatin, pyrrolo[1,4]benzodiazepine, indolinobenzodiazepine, or oxazolidinobenzodiazepine.

38. A pharmaceutical composition comprising the intact antibody or antigen binding fragment thereof of claim 36.

39. An anti-CD123 intact antibody or antigen binding fragment thereof comprising a heavy chain variable region having the amino acid sequence set forth in SEQ ID NO:1 provided that H20 is occupied by M or V, H38 is occupied by K or R, H48 is occupied by I, H66 is occupied by K or R, H67 is occupied by A, H69 is occupied by L, H71 is occupied by V, H73 is occupied by R, H81 is occupied by E or H, H82A is occupied by S or N, and H93 is occupied by T; and a light chain variable region having the amino acid sequence set forth in SEQ ID NO:2 provided that L2 is occupied by F, L19 is occupied by A or V, L21 is occupied by I or M, L22 is occupied by N or S, L38 is occupied by L.

40. The antibody of claim 39 wherein the heavy chain variable region is fused to a heavy chain constant region; and the light chain variable region is fused to a light chain constant region.

41. The intact antibody or antigen binding fragment of claim 39 conjugated to a cytotoxic agent.

42. The intact antibody or antigen binding fragment of claim 41 wherein the cytotoxic agent is a maytansinoid, auristatin, pyrrolo[1,4]benzodiazepine, indolinobenzodiazepine, or oxazolidinobenzodiazepine.

43. The intact antibody or antigen binding fragment of claim 42 wherein the cytotoxic agent is

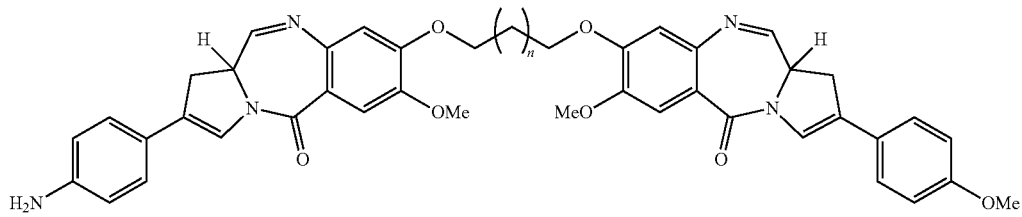

wherein the subscript n is 1 or 3; or a pharmaceutically acceptable salt thereof.

44. A pharmaceutical composition comprising the intact antibody or antigen binding fragment thereof of claim 41.

45. An isolated polynucleotide comprising a sequence encoding a heavy chain variable region having the amino acid sequence set forth in SEQ ID NO:1 and a light chain variable region having the amino acid sequence set forth in SEQ ID NO:2.

46. An isolated vector comprising the polynucleotide of claim 45.

47. An isolated host cell comprising the vector of claim 46.

48. The host cell of claim 47, wherein the host cell is a CHO cell.

49. A method of making an anti-CD123 antibody or antigen binding fragment thereof, wherein the method comprises:
   a) culturing the host cell of claim 47 under conditions suitable for expression of the polynucleotide encoding the antibody or antigen binding fragment thereof; and
   b) isolating the antibody or antigen binding fragment thereof.

50. The method of claim 49, wherein the host cell is a CHO cell.

51. A method of making an anti-CD123 antibody drug conjugate, wherein the method comprises:
   a) culturing the host cell of claim 47 under conditions suitable for expression of the polynucleotide encoding the antibody or antigen binding fragment thereof;
   b) isolating the antibody or antigen binding fragment thereof; and
   c) conjugating a cytotoxic agent to the antibody or antigen binding fragment thereof.

52. The method of claim 51, wherein the host cell is a CHO cell.

53. The method of claim 51, wherein the cytotoxic agent is a maytansinoid, auristatin, pyrrolo[1,4]benzodiazepine, indolinobenzodiazepine, or oxazolidinobenzodiazepine.

* * * * *

UNITED STATES PATENT AND TRADEMARK OFFICE
CERTIFICATE OF CORRECTION

PATENT NO. : 10,912,842 B2
APPLICATION NO. : 15/735738
DATED : February 9, 2021
INVENTOR(S) : Sutherland et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Thirty-first Day of January, 2023

Katherine Kelly Vidal
*Director of the United States Patent and Trademark Office*